(12) United States Patent
Kinjo

(10) Patent No.: US 7,115,365 B2
(45) Date of Patent: *Oct. 3, 2006

(54) METHOD OF ANALYZING A TARGET NUCLEIC ACID

(75) Inventor: Masataka Kinjo, Sapporo (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/325,189

(22) Filed: Jun. 3, 1999

(65) Prior Publication Data

US 2002/0146688 A1    Oct. 10, 2002

(30) Foreign Application Priority Data

Dec. 7, 1998 (JP) .................................. 10-347493
Dec. 11, 1998 (JP) .................................. 10-353254

(51) Int. Cl.
*C12Q 1/68* (2006.01)
*C12P 19/34* (2006.01)
*C07H 19/34* (2006.01)

(52) U.S. Cl. ...................... 435/6; 435/91.2; 536/25.32
(58) Field of Classification Search ............... 435/91.2, 435/6; 536/25.32
See application file for complete search history.

(56) References Cited

U.S. PATENT DOCUMENTS 4,965,188 A * 10/1990 Mullis et al. ................... 435/6
5,567,583 A * 10/1996 Wang et al. .................... 435/6
5,807,677 A * 9/1998 Eigen et al. .................... 435/6
6,391,544 B1 * 5/2002 Salituro et al. ................. 435/6

OTHER PUBLICATIONS

Gyllensten et al., generation of single-stranded DNA by the polymerase chain reaction and its application to direct sequencing of the HLA-DQA locus, Proc. Natl. Acad. Sci. USA, 1988, vol. 85, p. 7652-7656.*
Gyllensten et al., "Generation of single-stranded DNA by the polymerase chain reaction and its application . . . sequencing of the HLA-DQA locus", Pro. Natl. Acad. Sci., vol. 85, pp. 7652-7656 (1988).*
Clive et al., J. Neurosci. Methods, 1998, vol. 81, (1,2), p. 25-34.*
McCabe, PCR Protocol: A Guide to Methods and Applications, Part one, 1990, Chapter 10, p. 76-83.*

* cited by examiner

*Primary Examiner*—Kenneth R. Horlick
*Assistant Examiner*—Joyce Tung
(74) *Attorney, Agent, or Firm*—Frishauf, Holtz, Goodman & Chick, P.C.

(57) ABSTRACT

A biological sample containing a target nucleic acid is mixed with a primer, a substrate labeled with fluorescence, and DNA polymerase to prepare a test solution. After a nucleic acid amplification reaction is performed in a predetermined manner, the test solution is attached dropwise on a slide glass, which is mounted on a sample holder of an inverted fluorescence microscope. Data measured by a photomultiplyer are arithmetically operated by applying an autocorrelation function in a data processing apparatus. Based on the arithmetic results, quantification data for the target nucleic acid, are numerically or graphically displayed on a screen of a display apparatus.

9 Claims, 8 Drawing Sheets

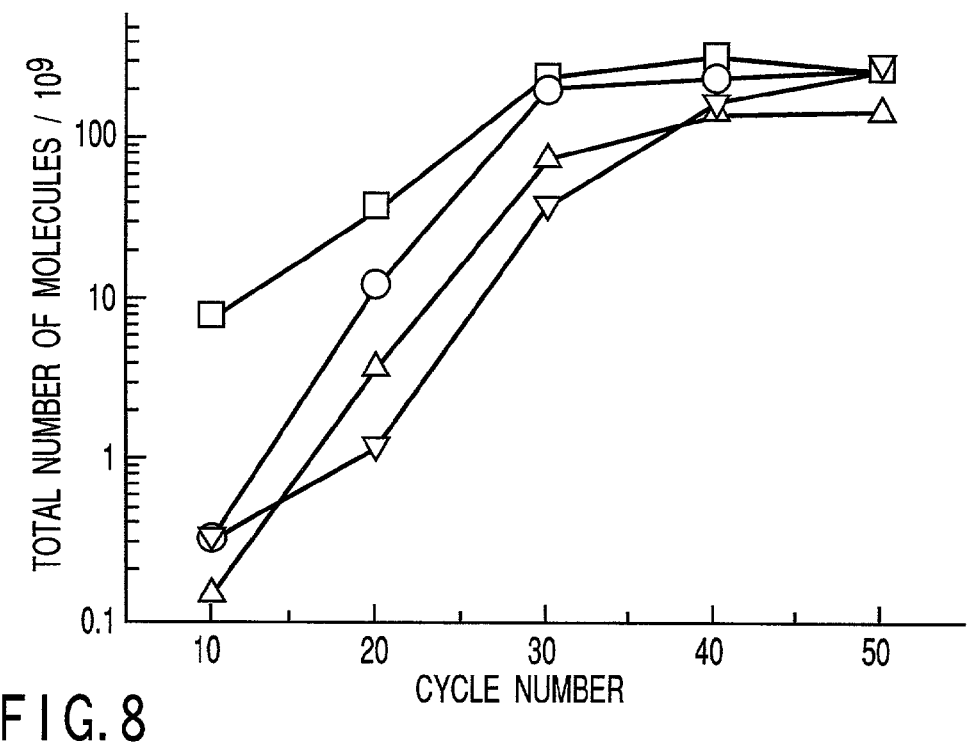
F I G. 8
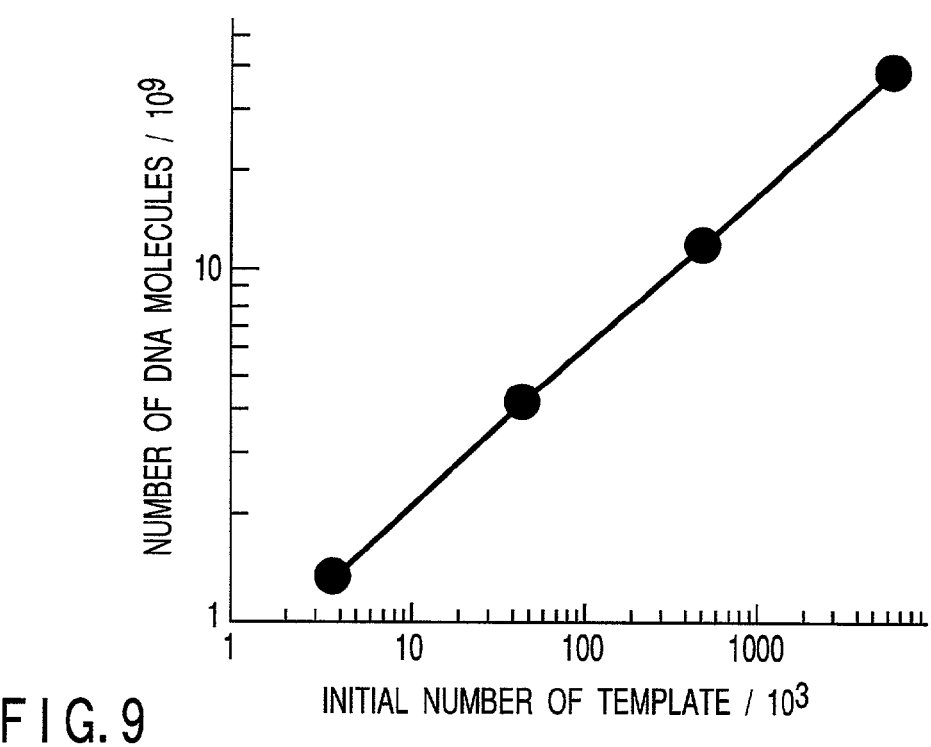
F I G. 9

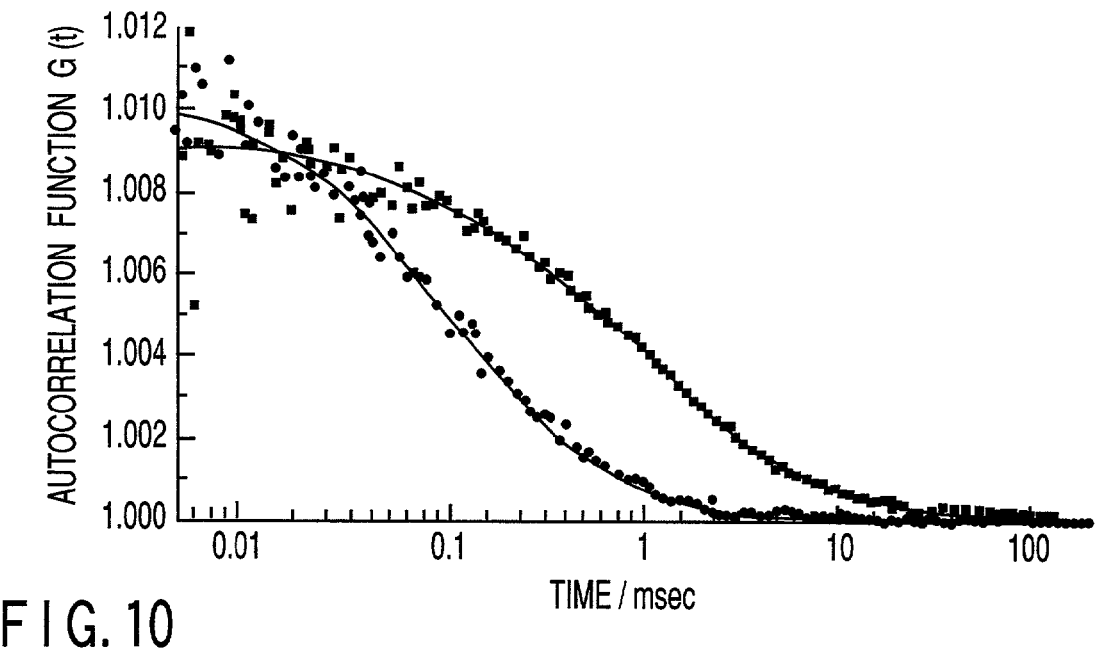
F I G. 10
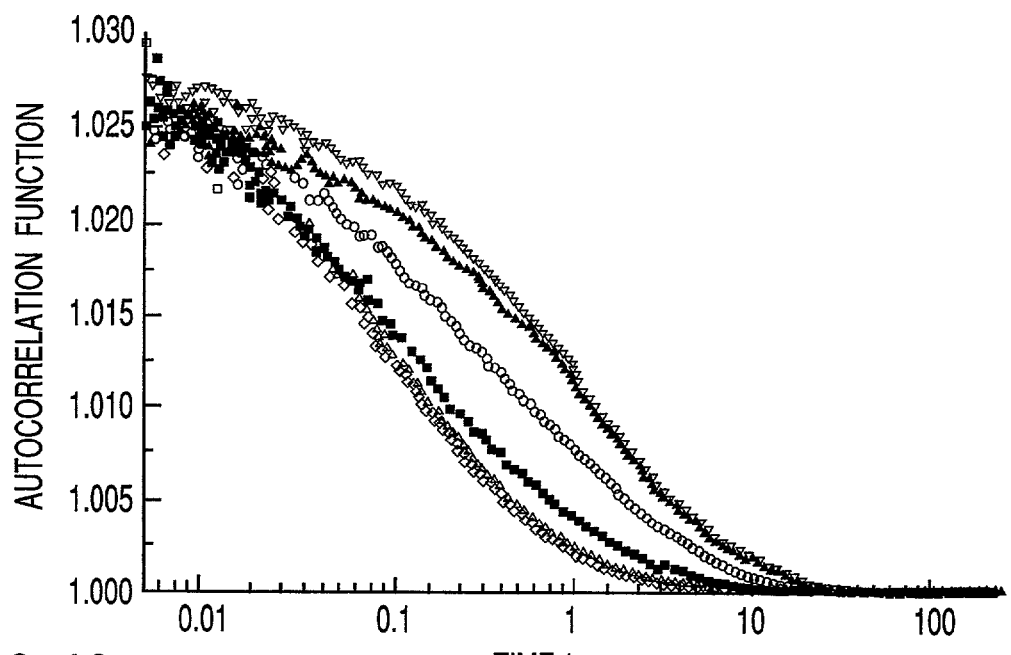
F I G. 12

SEQUENCE LISTING

```
<160> NUMBER OF SEQ ID NOS:  4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 1
gatgagttcg tgtccgtaca act                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 2
cttaaccagt gcgctgagtg act                                              23

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 3
gatgagttcg tgtccgtaca actgg                                            25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 4
ggttatcgaa atcagccaca gcgc                                             24
```

METHOD OF ANALYZING A TARGET NUCLEIC ACID

FIELD OF THE INVENTION

The present invention relates to a technique for analyzing a nucleic acid molecule present in a test sample, and more particularly, to a method for specifically measuring nucleic acid molecules amplified by applying a nucleic amplification method. The present invention is applied to a detection method in which measurement data with respect to a single nucleic acid molecule is valuable. Accordingly, the present invention can be effectively applied to any cases for the purpose of obtaining quantitative information regarding the number of target nucleic acid molecules.

BACKGROUND INFORMATION

Determination and detection of nucleotide sequences and measurement of molecular weights regarding nucleic acids such as DNA and RNA, are the most important analytical means in biochemical and molecular biological research, and recently, have also become an important tool in gene diagnosis and gene therapy. Generally, in the case where these analytical means are applied to biological test samples such as blood, urine, cerebrospinal fluid, and saliva, the analysis is performed after amplifying nucleic acid molecules present in an extremely small amount in the test sample to an appropriate concentration, in order to increase accuracy in the analysis. For example, in PCR (polymerase chain reaction), which is a very important gene amplification method, two types of primers work together in a plurality of amplification cycles. An amplified gene through appropriate amplification cycles is finally detected by subjecting the amplified sample to gel electrophoresis to separate them into fractions based on chain length (molecular weight), and then, determining the presence and absence of a fraction corresponding to a specific chain length.

In the PCR, a target nucleic acid is treated in the presence of DNA polymerase serving as a nucleic acid synthase, primers for initiating replication, and four types of bases (dATP, dGTP, dTTP, dCTP) serving as substrates for use in replication, under conditions in which a polymerizing reaction of the substrate molecules can take place. It follows that a complementary chain is synthesized by using a single-stranded DNA derived from the target nucleic acid as a template to form a double stranded DNA (dsDNA), resulting in amplification of the nucleic acid. As described, the PCR product amplified by co-working of two types of primers always forms a double stranded DNA (dsDNA).

The hybridization reaction using an oligonucleotide probe having a specific nucleotide sequence is used for determining a nucleotide sequence of the PCR product, namely, dsDNA. However, the hybridization reaction using the oligonucleotide probe has such problems that non-specific hybridization easily takes place because quick annealing must be repeated, and further, both DNA chains resemble the probe in nucleotide sequence.

As a quantitative method for measuring a total amount of dsDNA after amplified by the PCR method, some methods have been proposed hitherto. For instance, one of the methods is as follows. PCR is effected in a predetermined number of cycles using a sufficient amount of a PCR primer labeled with a marker molecule such as a fluorescent dye. The PCR product obtained through the predetermined cycles is subjected to electrophoresis to separate into a primer elongated by polymerase reaction and a free primer not elongated (Bound/Free separation). After the bound/free separation, a total number of fluorescent molecules is counted by a fluorometer. Also known is another method using, as the fluorescent marker, an intercalator (e.g. acridine orange, thiazole orange, oxazole yellow, etc.) which cannot emit fluorescence until it intercalates into the dsDNA during the amplification process. In this method, it is possible to measure the intensity of fluorescent which is emitted from dsDNA hybridized in a test solution only, without effecting the Bound/Free separation.

In the methods described above which measure a total fluorescent amount obtained from a whole test solution, the primers are used in a sufficient amount so as to cause no shortage of the primer during the nucleic acid amplification process of predetermined cycles regardless of an initial concentration of a target nucleic acid molecule. However, in the amplification reaction in the PCR method, various reaction curves are obtained depending upon not only the number (or amount) but also types of target nucleic acid molecules present in a test sample. It is therefore difficult for a conventional analytic method, which measures a total amount of the marker molecules attached to the amplified nucleic acids, to quantitatively monitor the reaction process. In particular, in the conventional PCR method, a signal derived from the free labeled molecules is eliminated and only a signal from the labeled primer hybridized with the target nucleic acid is measured, by removing free labeled molecules through the Bound/Free separation or by employing the intercalator. It is therefore impossible to monitor whether a particular free primer molecule is hybridized or not. Accordingly, in the conventional target nucleic acid analysis, it is impossible to perform quantitative analysis in the presence of a free primer molecule. Furthermore, since a total amount of fluorescence of the whole test solution is measured, the amount of the test solution must be increased in order to improve the sensitivity of the measurement. In addition, since the measurement cannot be performed until a nucleic acid is sufficiently amplified, it is almost impossible to detect a target nucleic acid in an earlier stage of amplification. More specifically, it is difficult to perform quantitative analysis for determining the number (or amount) of the target nucleic acids in the mid-stage of the PCR amplification process, let alone in the earlier stage of the process.

On the other hand, a technique has been lately developed for accurately determining micro-motions of individual target molecules by measuring fluctuation motion of the target molecule in fluid and applying an autocorrelation function. The method of this type is called as a fluorescence correlation spectroscopy (referred to as "FCS" hereinafter) since a fluorescent marker molecule is measured by an optical instrument. An arithmetical operation using the FCS for processing data regarding a biological material are disclosed by Kinjo et al., in which FCS is employed in a hybridization reaction between a labeled nucleic acid probe and a target nucleic acid molecule (Kinjo, M., Rigler, R., Nucleic Acids Research, 23, 1795–1799, 1995).

As a method for detecting a target gene by use of FCS, some reports have been recently provided. According to the report made by Oehlenschlager, F. et al. (Proc. Natl. Acad. Sci. USA, 93, 12811–12816, 1996), it is demonstrated that NASBA (Nucleic Acid Sequence Based Amplification) combined with FCS is an effective detection method for diagnosing HIV (Human Immunodeficiency Virus) in a serum. The NASBA method, which is a modified PCR method, requires an additional primer labeled with fluorescence as a probe other than two primers described above in the presence of three enzymes, i.e., T7 RNA polymerase, reverse transcriptase, and RNaseH.

As a more simplified method than the NASBA method, an amplified probe extension (APEX) using FCS has been reported from the same group (Walter, N. G. et al., Proc. Natl. Acad. Sci. USA, 93, 12805–12810, 1996). Even in the simplified method, an additional primer labeled with fluorescence is also required as a probe, besides a set of a forward primer and a reverse primer. In an experiment of APEX, change in autocorrelation function value with time is observed after 26 cycles.

However, in both the NASBA method and the APEX method, since an additional labeled probe is required besides the materials for use in general nucleic acid amplification, reaction conditions becomes complicated, making it difficult to stably control an accuracy of analysis. Furthermore, since the probe molecule is labeled with a single fluorescent marker, a signal derived from a labeled free probe significantly reduces an S/N ratio. As a result, the detection sensitivity tends to decrease as the initial concentration of the target nucleic acid molecule decreases. Furthermore, many cycles of PCR reactions must be performed to ensure the detection.

BRIEF SUMMARY OF THE INVENTION

The present invention was made in view of the aforementioned circumstances surrounding nucleic acid detection methods.

An object of the present invention is to provide a method of accurately and quantitatively detecting an amount of a target nucleic acid molecule by considering a labeled free molecule also as a measurement target. Another object of the present invention is to provide a method of quantitatively monitoring and measuring a PCR amplification reaction. Still another object of the present invention is to provide a method of quantitatively detecting a nucleic acid molecule even if the copy number is low. A further object of the present invention is to provide a method of detecting the presence and absence of the target nucleic acid molecule even if a small amount of test sample is available. A still another object of the present invention is to provide a method for detecting the presence and absence of the target nucleic acid in an earlier stage of the amplification process. A still further object of the present invention is to provide a method of measuring a nucleic acid molecule, capable of investigating a PCR amplification process at a molecular level.

To attain the aforementioned objects, according to a first aspect of the present invention, there is provided a method of analyzing a target nucleic acid by applying a nucleic acid amplification reaction to a test solution, the method comprises the steps of:

performing a nucleic acid amplification reaction of the target nucleic acid using a test solution containing a primer, substrate molecule at least one of which is labeled with a marker molecule capable of generating a detectable signal, a nucleic acid synthase, and a target nucleic acid molecule;

measuring a signal from the marker molecule in the test solution after initiation of the nucleic acid amplification reaction;

evaluating mobility of the labeled molecule in the test solution on the basis of the signal detected; and quantifying the target nucleic acid molecule on the basis of evaluation results.

According to a second aspect of the present invention, there is provided an apparatus of analyzing a target nucleic acid by applying a nucleic acid amplification reaction to a test solution, the apparatus comprises:

holding means for holding a test solution containing a primer, substrate molecules at least one of which is labeled with a marker molecule capable of generating a detectable signal, a nucleic acid synthase, and a target nucleic acid;

measuring means for measuring a signal from the marker molecule after initiation of a nucleic acid amplification reaction in the test solution;

evaluation means for evaluating mobility of the marker molecule in the test solution on the basis of the signal detected; and data output means for outputting a evaluation result obtained by the evaluation means as a quantification data of the target nucleic acid molecule.

According to a third aspect of the present invention, there is provided a method of quantitatively analyzing a target nucleic acid molecule present in a biological sample, comprising:

an amplifying step of amplifying the target nucleic acid by using first and second primer molecules having sequences which are complementary with two discrete nucleotide sequence regions of the target nucleic acid molecule respectively, at least one of the first and second primers being labeled with a detectable marker molecule and at least the number of labeled primer molecules being known;

a measurement step of obtaining measurement data regarding the labeled molecule by using at least a part of a test solution which has been subjected at least a single amplification step; and a determination step of determining a number and a size of the target nucleic acid molecules on the basis of the measurement data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 8 is a graph showing the number of amplified DNA molecules in a PCR reaction solution (5 μL) versus the PCR cycle number;

FIG. 9 is a graph showing the number of DNA molecules after 20 cycles versus the initial template number;

FIG. 10 is a graph showing a typical fluorescence autocorrelation function;

FIG. 12 is a graph showing fluorescence autocorrelation functions in the case that an initial template concentration before PCR in a reaction solution (25 μL) is changed from $1.9 \times 10^7$ to 1.9 for investigating the sensitivity of the method of the present invention;

DETAILED DESCRIPTION OF THE INVENTION

Figure 1:
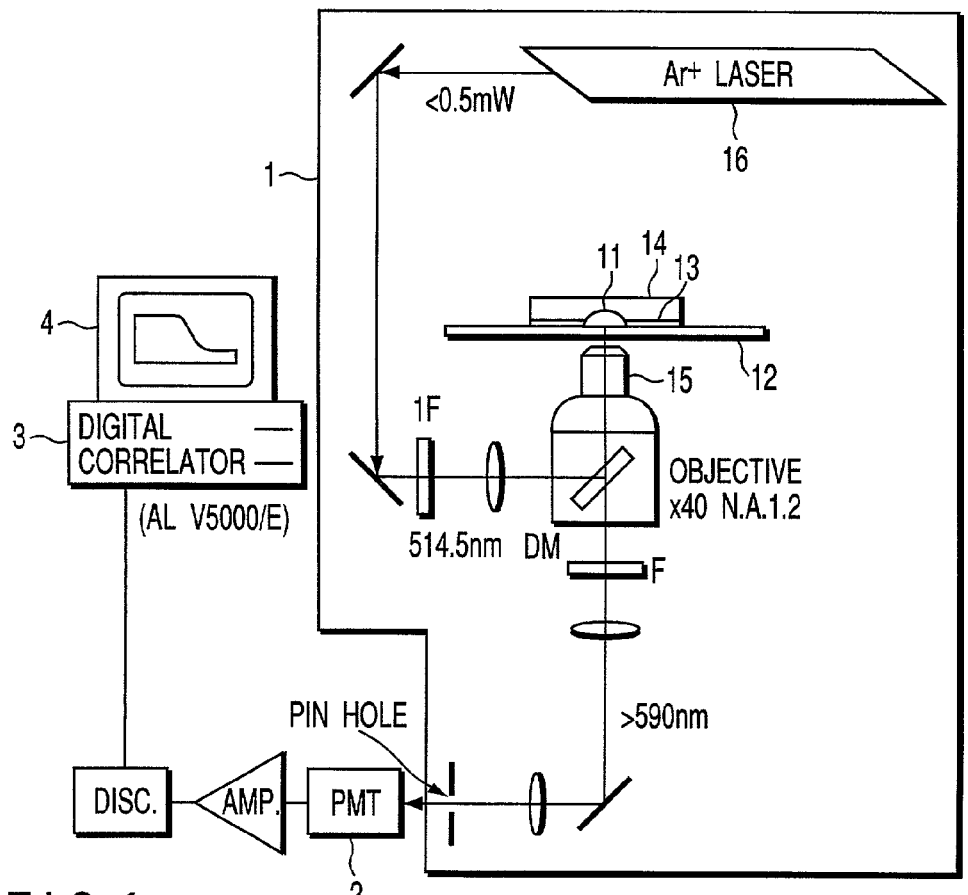
FIG. 1 is a schematic view showing an example of an apparatus for carrying out a method of the present invention.

Hereinafter, the present invention will be described in more detail.

In a preferred embodiment of the first and second aspects of the present invention, at least one of monomer nucleotides serving as substrates in the PCR reaction is labeled with a fluorescent marker, and this fluorescent-labeled monomer nucleotide is monitored.

To be more specific, the present invention has been made based on such a finding successfully demonstrated by image analysis rather than gel electrophoresis that when a target nucleic acid is amplified by using, as one of the monomer substrates, fluorescein-11-dUTP which is a monomer nucleotide labeled with a fluorescent dye molecule, the molecular weight of the target nucleic acid changes during the amplification process including the incorporation of the fluorescent monomer nucleotide.

Furthermore, the present invention has been made based on the finding that when the motion of the fluorescent dye molecule was evaluated by applying an autocorrelation function, quantitative results were obtained. Furthermore, the present invention is based on the finding that sensitivity was further improved without any adverse influence on measurement, by separating the labeled monomer nucleotide not incorporated into the amplification products during the nucleic acid amplification process, by using, for example, a gel filtration column.

According to a first aspect of the present invention, there is provided a method of analyzing a target nucleic acid by applying a nucleic acid amplification reaction to a test solution, the method comprises the steps of:

performing a nucleic acid amplification reaction of the target nucleic acid using a test solution containing a primer, substrate molecules at least one of which is labeled with a marker molecule capable of generating a detectable signal, a nucleic acid synthase, and a target nucleic acid molecule;

measuring a signal from the marker molecule in the test solution after initiation of the nucleic acid amplification reaction;

evaluating mobility of the labeled molecule in the test solution on the basis of the signal detected; and quantifying the target nucleic acid molecule on the basis of evaluation results.

The step of performing the nucleic acid amplification reaction is well known to the skilled in the art, and the nucleic acid synthase may be a polymerase or a reverse transcriptase.

It is preferred that the measurement step include a step of measuring an amount (number) of the marker molecule present in a predetermined measurement region. It is further preferred that, in the measurement step, a moving amount of the marker molecules within a predetermined time interval be measured for a plurality of time points. Furthermore, a step of removing the labeled substrate molecule not reacted in the nucleic acid amplification reaction may be included between the amplification reaction step and the measurement step. It is preferable that the measurement is performed in such condition that the measurement system is not in contact with the test solution, because the non-contact measurement not only improves sensitivity but also enhances the reproducibility of the measurement results without reducing accuracy.

It is preferred that the evaluation step described above includes a step of converting a plurality of measurement data into statistical data which express a change in the moving amount of the marker molecule. Furthermore, the conversion step preferably includes a step of performing arithmetic operation applying an autocorrelation function.

Furthermore, it is preferred that the quantification step described above includes a step of determining the presence and absence of the marker molecule incorporated into the amplified products during the nucleic acid amplification process based on the evaluation results. Furthermore, it is preferred that the quantification step includes a step of determining the amount (or number) of the labeled nucleic acids incorporated into the amplified products during the nucleic acid amplification process, based on the evaluation results.

According to a second aspect of the present invention, there is provided an apparatus of analyzing a target nucleic acid by applying a nucleic acid amplification reaction to a test solution, the apparatus comprises:

holding means for holding a test solution containing a primer, substrate molecules, at least one of which is labeled with a marker molecule capable of generating a detectable signal, a nucleic acid synthase, and a target nucleic acid;

measuring means for measuring a signal from the marker molecule after initiation of a nucleic acid amplification reaction in the test solution;

evaluation means for evaluating mobility of the marker molecule in the test solution on the basis of the signal detected; and data output means for outputting a evaluation result obtained by the evaluation means as quantification data of the target nucleic acid molecule.

It is preferred that the measurement means described above have an optical system for performing measurement within a micro detection field restricted in a diffraction-limited region near a focal point. Alternatively, the measurement means preferably have a microscope for attaining measurement in the micro detection field formed by a confocal optical system. It is further preferable that the diffraction-limited region be formed by means of an aperture having an average diameter of 30±20 µm. Furthermore, it is preferable that the diffraction-limited region be formed by means of an aperture having an average diameter of 20±10 µm.

It is preferred that the micro detection field be nearly a cylindrical region having an average radius of 200±50 nm and an average length on an optical axis of 2000±500 nm.

It is preferred that the evaluation means described above comprises a means for storing a plurality of measurement data obtained in a predetermined time interval and an arithmetic operating means for processing the plurality of measurement data stored by applying an autocorrelation function. Furthermore, it is preferred that the evaluation means comprise a means for storing measurement data with respect to a plurality of labeled molecules or the marker molecules obtained in a predetermined measurement region, and an arithmetic operating means for processing the stored measurement data with respect to each of the labeled molecules or the marker molecules by applying an autocorrelation function.

It is further preferable that the data output means described above comprise a conversion means for converting the arithmetically processed results obtained by applying the autocorrelation function into statistical data which express a positional change with time of each labeled molecule corresponding to a plurality of monitoring data.

In the method according to the first aspect of the present invention, at least one type of substrate molecules which will be incorporated into the amplified products during the nucleic acid amplification process of the PCR is labeled with a marker molecule capable of generating a detectable signal. The substrate molecule, i.e., monomer nucleotide having such a marker molecule is maintained free during a hybridization between the target nucleic acid and the primer for PCR initiation. In the nucleic acid synthesis process following the hybridization, when the nucleic acid synthase works on the primer hybridized to the target nucleic acid molecule, the substrate molecules are sequentially incorporated into the primer for extending the primer to the amplified product. The marker molecule which is incorporated together with the substrate molecule into the amplified product during the nucleic acid amplification process, decreases in mobility in the test solution, as compared to the marker molecule bonded to the free substrate molecule.

Then, at least a part of the test fluid which contains amplified product from efficient PCR cycles is quantitatively taken as an aliquot in the holding means and subjected to the measurement of the marker molecule. The holding means for the test solution used herein may be a concave-form container such as a test tube, a well, or a Petri dish, or a flat-plate holder such as a slide glass. Depending on the situation, the test fluid may be held by directly adhering it as a drop on the surface of the measurement means. Alternatively, the test fluid contained in a PCR reaction container may be subjected to the measurement as it is.

Any measurement means may be employed as long as it can measure a change in size of the molecule carrying the marker during nucleic acid amplification process. For example, gel electrophoresis, capillary electrophoresis, flow-cytometer for fluorescence measurement, image cytometer, and fluorescence microscopy or the like may be effectively used. When the measurement step is performed in a three dimensional micro detection field, free micro-motion of the labeled molecule in the test fluid can be accurately determined while keeping its natural state corresponding to the results of PCR reaction. The micro detection field can be optically designed, for example, by converging light from a halogen lamp or by emitting light through an aperture having an extremely small average radius. In this case, it is preferable to use converged laser light.

When the micro detection field is formed by a confocal optical system in the measurement step, measurement data can be obtained with a deep depth of field. As a result, individual arbitrary marker molecules are always brought into focus in the detection field so that accurate positional data and fluorescent output data can be supplied to the measurement means.

If the micro detection field falls within the diffraction limited region near a focal point, the individual marker molecules can be measured with a high S/N ratio.

If the diffraction limited region is formed by a pin hole having an average diameter of 30±5 µm, measurement data of a small number of selected marker molecules can be efficiently obtained.

When the micro detection field is formed in nearly a cylindrical form having an average radius of 200±50 nm and an average length on the optical axis of 2000±500 nm, it is possible to capture the free micro-motion of the marker molecule sighted in the measurement detection field.

In the present invention, the speed of the marker molecule moving in and out of the micro detection field is measured by using, as an indication, increase/decrease or appearance/disappearance of output signal intensity from at least one marker molecule present in a predetermined space. Accordingly, the preferred marker molecule to be tagged to the substrate molecule is that capable of outputting a constant signal at a plurality of measurement points. The preferred marker molecule includes luminescent material, fluorescent material, magnetic material, radioactive material and the like. In particular, as the luminescent material and fluorescent material, a dye that emits luminescence or fluorescence for a long time may be preferable. If the marker molecule having a luminous dye or a fluorescent dye is used, measurement of molecular level can be effected by using a simple optical system. As the fluorescent dye, there are well known dyes such as DAPI, FITC, rhodamine, Cy 3, Cy 3.5, Cy 5, Cy 5.5, Cy 7 and the like.

When mobility of the fluorescence molecule is measured in the measurement step, fluorescent light is received by a fluorescence measurement means such as a photo-multiplyer or a photo-diode. The fluorescence measurement means having a measurement mode capable of measuring a single photon is advantageous because it enables to measure individual fluorescent molecules.

It is possible to attain the accurate measurement of each marker molecule in a more effective embodiment in which the fluctuation motion of the marker molecule in a fluid is measured in the measurement step. In the case where the fluctuation motion is measured, an arithmetic operation may be preferably performed by applying an autocorrelation function. In particular, when fluorescent a molecule is used as the marker molecule, it is preferred that fluorescence correlation spectroscopy (simply referred to as "FCS" hereinafter) be used. In arithmetically operating the measurement data of biological material by using FCS, reference can be made to a report by Kinjo et al. in which FCS is used in a hybridization reaction between a labeled nucleic acid probe and a target nucleic acid molecule (Kinjo, M., Rigler, R., Nucleic Acids Research 23, 1795–1799, 1995).

An apparatus for performing FCS is schematically shown in FIG. 1. The FCS apparatus comprises an inverted fluorescence microscope 1 using a confocal optical system, a photo-detector such as a photomultiplier 2 for measuring fluorescence from a test sample, a data processing apparatus 3 for receiving measurement data from the photo-multiplier 2 and performing an arithmetic operation by applying an autocorrelation function, thereby indicating the measurement data numerically or graphically, and a display apparatus 4 for displaying the result of the arithmetic operation on a screen.

A test sample fluid 11 can be simply set on a slide glass 13 mounted on a sample holder 12 by attaching the fluid thereon dropwise, as shown in FIG. 1. In this apparatus, since the test sample fluid 11 is used in an extremely small amount, a cover 14 is placed on a slide glass 13 in order to prevent vaporization of a moisture content of the fluid. It is preferred that the cover 14 is formed of a material with a minimum light transmissivity, since airtightness and light shielding properties can be simultaneously obtained. However, the inner surface of the cover may be preferably formed of a material with a minimum light reflectance in order to prevent reflection of an excitation light beam. Immediately under the portion of the slide glass 13 on which the test sample fluid 11 is placed, an object lens 15 is mounted in such a way that the focus is achieved in the test sample fluid 11.

Note that the fluorescence microscope 1 used herein may be a reflection-type fluorescent microscope. In the reflection-type fluorescent microscope, the test sample-containing fluid 11 may be directly attached dropwise on the lower surface of the objective lens 15. In FIG. 1, argon (Ar) ion laser is used as the laser generating apparatus 16 which serves as a light source for the fluorescent microscopy 1. However, the light source may be varied depending upon a type of fluorescence. More specifically, a krypton-argon (Kr—Ar) ion laser, helium-neon (He—Ne) laser, and helium-cadmium (He—Cd) laser may be used. In addition, various operations including loading/unloading of the slide glass 13 into/from the fluorescence microscope 1, dropwise attachment of the test sample fluid on the slide glass 13, and open/shut operation of the cover 14, may be performed automatically, if necessary.

Figures 2A, 2B:
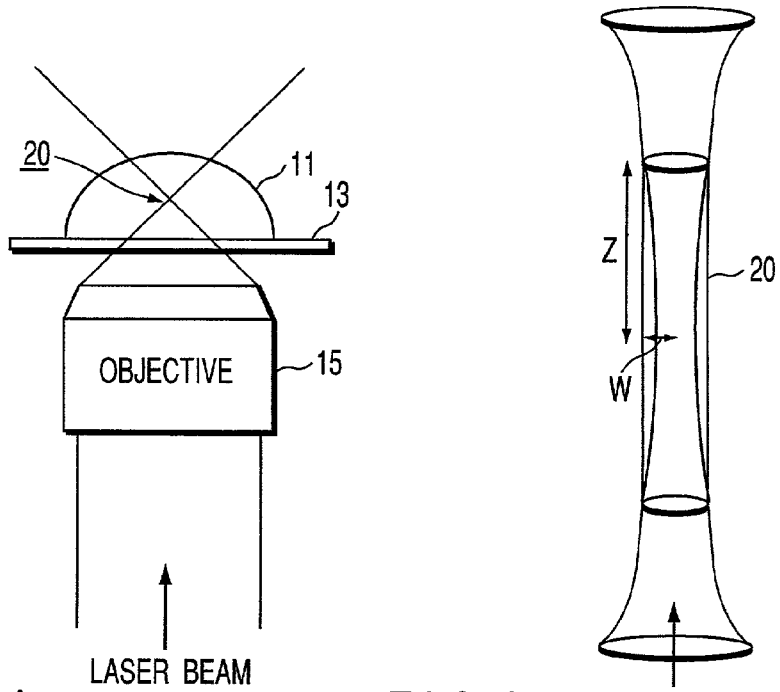
FIG. 2A is a partially enlarged view of the apparatus shown in FIG. 1.
FIG. 2B is an enlarged schematic view showing a microfield of the view in FIG. 2A.

FIG. 2A is an enlarged view showing a measurement portion of the fluorescence microscope 1. In FIG. 2A, a micro detection field 20 is formed by appropriately arranging positions of the slide glass 13 and an objective lens 15 having a predetermined numerical aperture (NA=1.2 in the figure). Actually, as shown in FIG. 2, the micro detection field 20 forms nearly a cylindrical region having a certain volume, which extends up and down from a focal point of the laser beams (a tightened middle portion). The detection field 20 is defined by a length Z along the optical axis and an average radius W from a focal point (reference point). If the micro detection field 20 is reduced to a minimum level for monitoring the micro-motion of the fluorescent molecules, it is possible to measure individual fluorescent molecules accurately since noise derived from the fluorescent molecule (in the test sample fluid 11) not present near the focal point can be efficiently eliminated.

A third aspect of the present invention relates to a similar analytical method to the first aspect except that the marker molecule is conjugated to the primer for PCR rather to the substrate molecule.

According to the third aspect, there is provided a method of quantitatively analyzing a target nucleic acid molecule present in a biological sample, comprising:

an amplifying step of amplifying the target nucleic acid by using first and second primer molecules having sequences which are complementary with two discrete nucleotide sequence regions of the target nucleic acid molecule respectively, at least one of the first and second primers being labeled with a detectable marker molecule and at least the number of labeled primer molecules being known;

a measurement step of obtaining measurement data regarding the labeled molecule by using at least a part of a test solution which has been subjected at least a single amplification step; and a determination step of determining a number and a size of the target nucleic acid molecules on the basis of the measurement data.

In the third aspect, a mixing ratio of the first primer and the second primer is not equal. In this respect, reference can be made to an asymmetric PCR method disclosed by Gyllenaten, U. B. et al. (Proc. Natl. Acad. Sci. USA 85, 7652–7656, 1988). However, the asymmetric PCR method disclosed by Gyllenaten, U. B. et al., is directed to production of a single stranded DNA (SSDNA) as a PCR product in order to simplify the determination of the nucleotide sequence. Therefore, in the asymmetric PCR, if the PCR is performed by using two types of PCR primers in an asymmetric ratio (that is, they are not contained in an equi-molar amount), after the minor primer is completely consumed during the PCR cycle, only ssDNA is produced in every following PCR cycle. The present invention is unique in that the asymmetric PCR method is modified in order not to determine the nucleotide sequence but to quantitatively determine the target nucleic acid. More specifically, in the present invention, a nucleic acid amplification reaction is performed by binding a marker molecule to the minor primer, and measuring a signal derived from the marker molecule bounded to the minor primer. Therefore, even when hybridization probabilities of the minor and major primers to the target nucleic acid are not equal, it is possible to securely and completely eliminate free marker molecules without performing the Bound/Free separation such as centrifugal separation or gel electrophoresis. As a result, the S/N ratio becomes extremely high. By virtue of the high S/N ratio, the present invention brings an epoch making effect of attaining quantitative analysis of a nucleic acid with a high detection sensitivity. Accordingly, the method of the present invention also makes it possible to detect the target nucleic acid molecule during or prior to the PCR amplification with a high accuracy.

Figure 3:
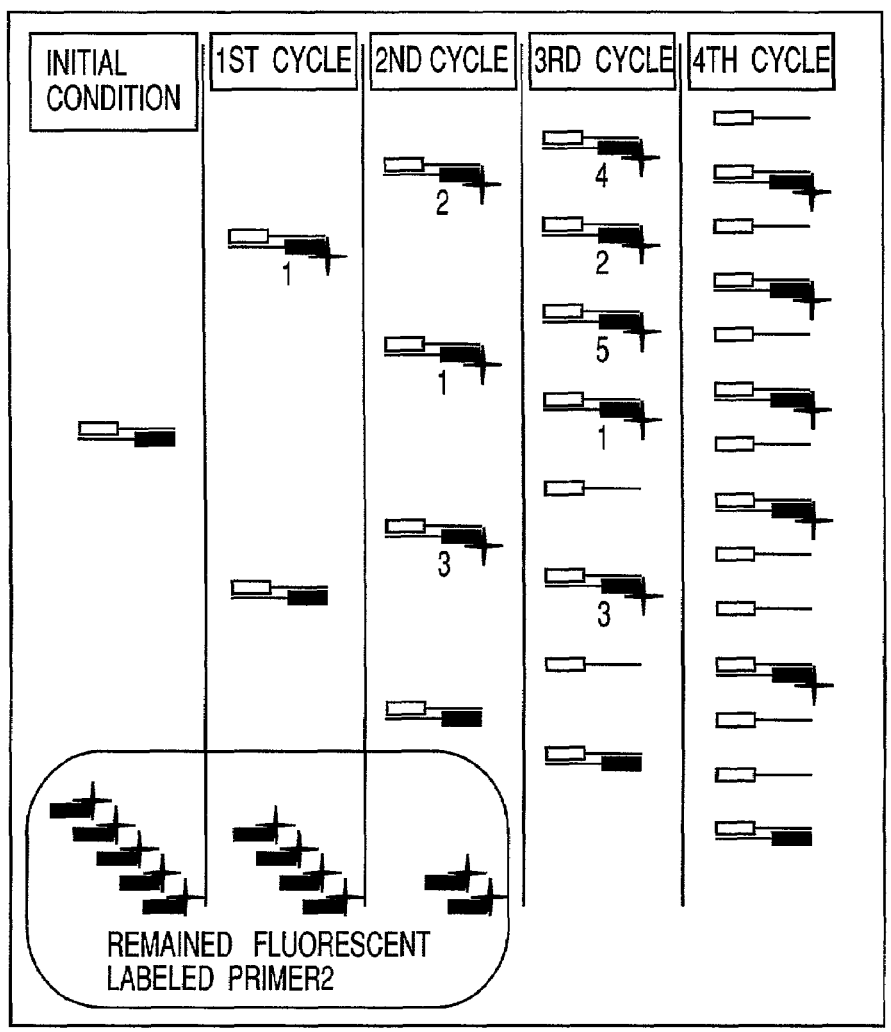
FIG. 3 is a schematic diagram of asymmetric PCR according to the present invention.

In the unique asymmetric PCR performed in the present invention, it is important that the amount of the second primer is set smaller than that of the first primer and that the second primer is labeled with an optically detectable marker molecule. As to the numbers of first and second primer molecules, it is preferable that the lowermost values thereof be set such that at least one cycle of the amplification cycle is effected under the presence of an excessive amount of the labeled primer molecules. Furthermore, as shown in a conceptional diagram (FIG. 3) of the unique asymmetric PCR according to the present invention, the number (or amount) of the second primer molecules which are labeled with markers is a critical factor to determine necessary repeats of the hybridization cycle in the unique asymmetric PCR. FIG. 3 shows the case where five second primer molecules are mixed with an excessive amount of the first primers, per target nucleic acid molecule. The amplification reaction step of this case is preferably performed in a certain mixing ratio of the first and second primer molecules, which is selected so as to attain the asymmetric nucleic acid amplification. In particular, it is further preferable that one of the primers be contained in a smaller number of moles than that of the other primer, and that the minor primer be labeled with the marker molecule. The mixing ratio of two types of primers contained in the test fluid preferably falls within the range of 2:1 to 20:1, since the production efficiency in the amplification reaction becomes high within this range. Furthermore, a mixing ratio in concentration of two types of primers in the test fluid preferably falls within the range of 800 nM:400 nM to 800 nM:40 nM, since the yield of the PCR product becomes high within this range.

In the amplification reaction applying the unique asymmetric PCR of the present invention, it is preferable that even if a test sample contains a large amount of the target nucleic acid, at least one cycle of the amplification reaction can be carried out completely without causing a shortage of the second primer. In the method of the present invention, it is possible to detect the target nucleic acid even when the target nucleic acid is present in a small amount. Therefore, the second primer can be further reduced if the test sample containing fluid is reduced. The number (or amount) of the second primer molecules may be statistically determined such that one or more PCR cycles are completely effected even when the target nucleic acid is present at the uppermost amount which may naturally occur in a test sample subjected to PCR. Hence, in case that the amplification reactions are performed using the target nucleic acid molecules in various amounts and the second primer in a constant amount, when the smaller amount of the target nucleic acid molecule is used, the more cycles must be repeated until they reach the satisfactory level of amplification, i.e., until the second primer is completely consumed. Therefore, it is preferred that the amount of the second primer is set such that the second primer is consumed in an appropriate PCR cycles even if only one target nucleic acid molecule is present in the test sample subjected to the measurement. As is apparent from FIG. 3, the amount of the second primer and the amount of the target nucleic acid contained in the test sample fluid have an influence on the time or number of PCR cycles required until the asymmetric PCR amplification reaction reaches a plateau or saturated. In the present invention, it is supposed that when the amount of either the first or second primer is set at a relatively significantly lower amount, the number of the primer molecules thus set lower should be known. If the known number of the primer molecules is small, both primers may be labeled with the same marker molecule. Accordingly, at least one of the first and second primers may be labeled in this case. On the other hand, since the major primer does not directly contribute to the measurement of the present invention, it is principally unnecessary to know the number of the major primer molecules.

After completion of effective cycles of PCR, at least a part of the test sample fluid is taken as an aliquot and subjected to measurement appropriately. Alternatively, the measurement may be carried out on the test fluid mixture contained in a PCR reaction container or the like. Any measuring method may be used as long as it can measure a change in size of the labeled molecule in the course of amplification. For example, gel electrophoresis, capillary electrophoresis, flow-cytometer for fluorescence measurement, image cytometer, and fluorescence microscopy may be effectively used. If the measurement step is performed in a three dimensional micro detection field, free motion of the labeled molecule in the test sample fluid can be accurately determined while keeping its natural state, in accordance with the results of the PCR reaction. The micro detection field can be formed by converging light from a halogen lamp or by passing the light through an aperture (pinhole or monomode fiber end) having an extremely small average radius. However, in this case, converged laser light is preferably used. More particularly, it is preferred to use an optical system in which an objective lens with an appropriate magnification and numerical aperture is employed so that the focal point is formed on an appropriate position within the test fluid.

If the micro detection field of the measurement step is formed by a confocal optical system, measurement data having a deep depth of field can be obtained. As a result, any individual marker molecules are always brought into focus in the detection field, and the accurate position of the marker molecules and output data of fluorescence can be supplied to the measurement means.

If the micro detection field falls within a diffraction limited region near a focus, the individual marker molecules can be measured with a high S/N ratio.

When the diffraction limited region is formed by a pin hole having an average diameter of 15±5 µm, measurement data can be efficiently obtained from a small number of selected marker molecules.

When the micro detection field is a nearly cylindrical area having an average radius of 200±50 nm and an average length on the optical axis of 2000±500 nm, it is possible to efficiently capture the free micro-motion of the marker molecule sighted in the measurement detection field.

In the present invention, mobility of the marker molecules moving in and out of the micro detection field is measured by using increase/decrease or appearance/disappearance of the intensity of signal output from each marker molecule present in a predetermined space. Accordingly, the type of the marker molecule to be tagged to the second primer molecule is preferably capable of outputting a constant signal at a plurality of measurement time points. As the material to be used as the marker molecule, there are a luminescent material, fluorescent material, magnetic material, radioactive material and the like. In particular, as the luminescent material and fluorescent material, a dye that emits luminescence or fluorescence for a long time may be preferably selected. If the marker molecule having a luminescent dye or a fluorescent dye is used, measurement can be performed at a molecular level by using an apparatus having an optically simple structure. As a preferable fluorescent dye capable of emitting a detectable signal before and after the hybridization, there are FITC, rhodamine, DAPI, Cy 3, Cy 3.5, Cy 5, Cy 5.5, Cy 7 and the like.

When a positional change of the fluorescence molecule is measured in the measurement step, fluorescent signal can be received by a fluorescence measurement means such as photo-multiplyer or photo-diode. The fluorescence measurement means that has a measurement mode capable of measuring a single photon, is useful for measuring individual fluorescent molecules.

When fluctuation motion of the marker molecules in a fluid is measured in the measurement step, the present invention will be a more effective embodiment since the micro-motion of each of marker molecules is accurately measured. In the case where the fluctuation motion is measured, arithmetic operation can be preferably performed by applying an autocorrelation function. In particular, when a fluorescent dye is used as the marker molecule, it is preferred that fluorescence correlation spectroscopy (simply referred to as "FCS") be used. The FCS measurement data of a biological material may be arithmetically operated with reference to a report made by Kinjo et al. in which FCS is used in a hybridization reaction between a labeled nucleic acid probe and a target nucleic acid molecule (Kinjo, M., Rigler, R., Nucleic Acids Research 23, 1795–1799, 1995).

The present inventor found that quantitative measurement of PCR is possible by using FCS in his own investigation. In his investigation, PCR was performed by using two types of primers in an equal amount, and by conjugating a fluorescent marker molecule to dUTP which is one of nucleotide monomers used in PCR amplification. As a result, the target nucleic acid molecule was able to be detected even if PCR was repeated in a small number of cycles. However, in the method thus found, it was necessary to perform a step for removing the fluorescent molecule not incorporated into the amplification product before the fluorescence measurement. Then, the present inventor further investigated and found a new method capable of quantifying the target nucleic acid molecule by PCR without removing the unbound marker molecule.

An apparatus for performing FCS analysis is as explained above in connection with FIGS. 1, 2A and 2B, so that the explanation thereof will be omitted herein.

Based on the aforementioned various embodiments, the present invention is applicable to diagnosis for genetic disease, parent-child identification, criminal examination, gene treatment, molecular biology research, development of medicinal products, and the like. It should be appreciated that the aforementioned embodiment may altered and modified without departing from the scope of the present invention. For example, in a measurement apparatus explained in the aforementioned embodiments, a test sample is placed on a holder and measured under the fluorescence microscope in the same manner as the microscope observation. However, if an apparatus disclosed in European Patent Publication No. 640828A1 is optically improved in such a way that the laser light emitted through an objective lens is focused on the test sample fluid within a thermal cycler, the amplification reaction can be continuously evaluated without transferring the test sample fluid onto a slide glass. A plurality of data may be obtained in the course of the PCR cycle, either continuously or intermittently in a predetermined time after completion of a predetermine cycle. Alternatively, an appropriate number of measurement data may be obtained in every different cycle.

Now, the present invention will be illustrated by way of examples, but the examples should not be construed any way to limit the present invention. The present invention may be modified in various ways on the basis of the gist of the present invention and within the scope obvious from the state of the art at the time of the present invention.

EXAMPLE 1

(1) PCR Under the Presence of Fluorescence-labeled Nucleotide

As a test solution, a mixture solution was prepared which contained 0.1 U$\mu$L$^{-1}$ of Pol I type DNA synthase (AmliTaq Gold, Perkin-Elmer), 1× buffer I (Perkin-Elmer), 200 $\mu$M of dATP, dGTP and dCTP, and 120 $\mu$M of dTTP, 80 $\mu$M of fluorescein 11-dUTP (FluoroGreen, Amersham Flu-dUTP), and 0.8 $\mu$M of a forward primer and a reverse primer. Then, using 5 $\mu$L and 25 $\mu$L of the test solution, a standard amplification of a nucleic acid was performed.

As a template, a lambda phage DNA having a total length of 48.5 kb was used in an amount of 200 pg/5 $\mu$L. The length of a target DNA was 4000 bp. The nucleotide sequence of the primers used in the nucleic acid amplification were as follows:

```
Forward primer:  GATGAGTTCGTGTCCGTACAACT
                 (SEQ ID NO: 1)
                 (nucleotide number = 7131–7153)
Reverse primer:  CTTAACCAGTGCGCTGAGTGACT
                 (SEQ ID NO: 2)
                 (nucleotide number = 11098–11120)
```

As a PCR apparatus for performing the nucleic acid amplification reaction, a programmable thermal control system (PC700, Astec Co. Ltd.) was used. As a PCR container storing each aforementioned test fluid, an oil-free reaction tube (Takara Shuzo Co., Ltd.) was used. First, a denaturation treatment (initial denaturation treatment) was performed at 96° C. for 15 minutes. Thereafter, predetermined PCR cycles each consisting of an annealing treatment (incubation at 55° C. for 15 minutes), an elongation reaction (incubation at 65° C. for 4 minutes) and a denaturation treatment (incubation at 96° C. for 1.5 minutes), were performed. After completion of the predetermined PCR cycles, the PCR container was removed from the PCR apparatus and stored at −20° C. until next use.

To eliminate nucleotides not incorporated into the amplified product, distilled water was added to each of test solutions after the PCR reaction, to a final volume of 50 $\mu$L, and each of the resultant mixture solutions was subjected to a MicroSpin column (S-400HR, Pharmacia Biotech Co., Ltd.). The volume Vc of each of the solutions collected by the column was measured based on the weight thereof, the volume Vc ranged from 55 $\mu$L to 60 $\mu$L. The solutions were further subjected to FCS measurement without purification. Assuming that a molecular weight of a single base pair was 660 Da, a molecular weight of the lambda phage DNA became 32×10$^6$ Da by calculation.

(2) FCS Measurement

Using the FCS apparatus shown in FIG. 1, FCS measurement was performed. A part of the test solution previously subjected to the nucleic acid amplification was used as a test sample. The test sample was attached dropwise on a sample slide glass. The sample slide glass was mounted on a sample holder of a commercially available FCS apparatus (Confo-Cor, CarlZiss Jena GmbH). The test sample was excited by CW Ar$^+$ laser beam passed through an objective lens (C-Apochromat, NA=1.2) of a 40× magnification. An emitted fluorescence light was measured by using Avalanche photo Diode (APD) (SPCM-200-PQ, EG&G) in a single photon counting mode. The fluorescence signal thus measured was analyzed and evaluated by a digital correlator (ALV5000/E (ALV GmbH)). It should be noted that the test sample actually subjected to the measurement was attached dropwise onto a cover glass in an amount of 20 $\mu$L and a small box was placed on the sample holder so as to cover the cover glass for preventing vaporization during the measurement. The sample volume at the region near a focal point was determined by using a diffusion count of rhodamine 6G. The volume element was determined by using concentrations of the fluorescein and Flu-dUTP solution.

The fluorescence signal was measured about every minute. Analytical evaluation was performed by programming so that the obtained fluorescence signals were sequentially stored in a memory section and applied to a fluorescence autocorrelation function G(t). The value of fluorescence autocorrelation function G(t) was calculated from an average number N of fluorescence molecules within a detection region, translational time $\tau_{mono}$ of a labeled free substrate molecule (Flu-11-dUTP), namely a nucleotide monomer (monomer DNA), and translational time $\tau_{poly}$ of a labeled substrate molecule incorporated into the amplification product, namely a polymer DNA, by use of the following Equation 1 based on a method disclosed by Rigler et al. (see Fluorescence Spectroscopy-New Methods and Applications, Springer, Berlin 13–24, In J. R. Lakowicz (Ed.), 1992):

$$G(t) = 1 + \frac{1}{N}\left[\left\{\frac{1-y}{1+\frac{t}{\tau_{free}}}\sqrt{\frac{1}{1+S^2 \cdot \frac{t}{\tau_{free}}}}\right\} + \left\{\frac{y}{1+\frac{t}{\tau_{poly}}}\sqrt{\frac{1}{1+S^2 \cdot \frac{t}{\tau_{poly}}}}\right\}\right]$$

Equation 1

In Equation 1, y is a ratio of the polymer DNA; $\tau_{mono}=Wo^2/4D_{mono}$, $\tau_{poly}=Wo^2/4D_{poly}$, $S=Wo/Zo$, wherein, Wo is a diameter of a volume element of nearly a cylindrical measurement region formed in the micro detection field (see, FIG. 2B), and 2Zo is a length of the volume element. $D_{mono}$ and $D_{poly}$ are translational diffusion coefficients of the monomer DNA and the polymer DNA, respectively.

Data analysis was performed by applying a non-linear least square parameter method for calculating a normalized average square deviation between the data and a model. The total number T of the molecules amplified through a desired PCR cycle was calculated by applying Equation 2 and was output as quantified data.

$$T=(N/Vo)Vc \quad \text{Equation 2}$$

wherein Vo is a volume element and Vc is a volume of a solution collected by a spin column. During the FCS measurement, an average fluorescence intensity was also measured. The intensity reflects the total number of fluorophores (Flu-dUTP) incorporated into the DNA amplified in the volume element. The value obtained by dividing a count rate of an average fluorescence intensity by the number of the DNA molecules (Ny) was employed as an average count rate (C/M) of the DNA molecules. The value was able to be used in practice as an effective marker concentration of the PCR products.

(3) Calculation of Measurement Region

The volume element of the measurement region was determined by measuring diffusion times of reference samples such as rhodamine 6G, fluorescein, and Flu-dUTP. A ratio of length to diameter of the measurement region (see FIG. 2B) formed near a focal point was obtained from the value of S in Equation 1. The ratio was about 0.2. The volume element $V_O$ was obtained as $1 \times 10^{-15}$ L through calculation.

(4) Incorporation of Flu-ll-dUTP into PCR Products

Figure 4A:
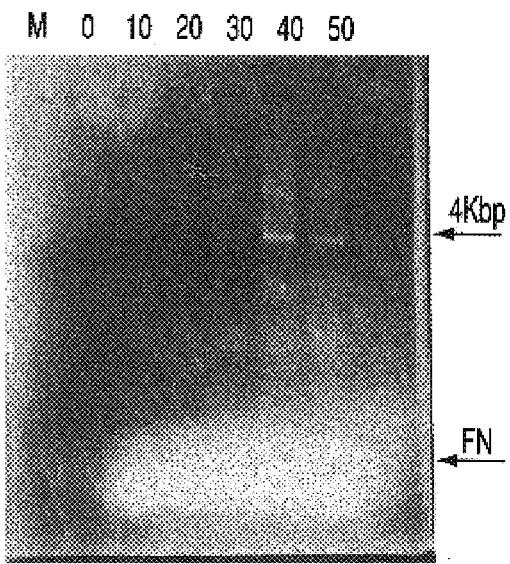
FIGS. 4A and 4B are electrophoretic (agarose) photographs each showing characteristics of an amplified product (4 kb)
Figure 4B:
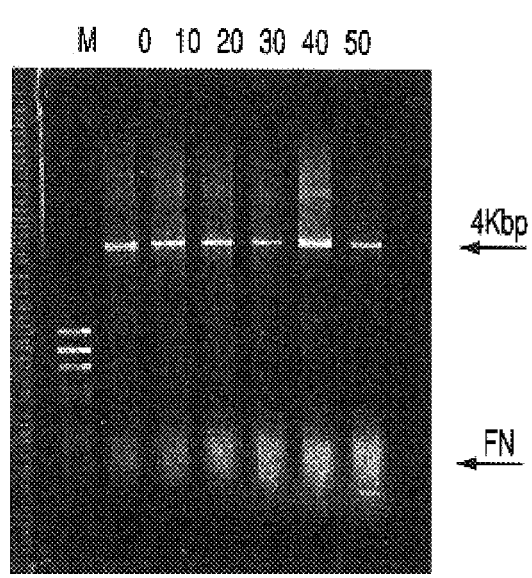

In order to elucidate a functional effect of fluorescence-labeled nucleotide in PCR, a concentration of Flu-dUTP was changed from 10% to 50%. FIGS. 4A and 4B are electrophoretic (agarose gel) photographs showing characteristics of amplified 4 kb products. More specifically, 3 μL of a PCR reaction mixture obtained after 50 cycles of the nucleic acid amplification was subjected to electrophoresis on 7% agarose gel. FIG. 4A is a photograph before staining with ethidium bromide, whereas FIG. 4B is a photograph after staining with ethidium bromide. In the figures, M denotes a molecular marker (Hae III-digested φx174 DNA). In the figure, numerals "0", "10", "20", "30", "40" and "50" indicate a percent ratio of dUTP to dUTP+dTTP. A symbol "FN" denotes a free Fluorescent Nucleotide (not incorporated into PCR product). When the fluorescence emitted from the gel was measured, an orange-colored optical filter Ya3 was used in FIG. 4A and a red-colored optical filter R1 was used in FIG. 4B.

According to FIG. 4A, a fluorescent PCR product of 4000 bp was able to be synthesized under the presence of 50% Flu-dUTP. The fluorescent intensity of the labeled DNA increased with the increase of concentration of Flu-dUTP. The total production amount of the amplified DNA can be exhibited by ethidium staining. This experiment demonstrated that the total production amount is the same in the case where no Flu-dUTP was contained.

(5) Fluorescence Intensity and Amplification Product Amount in PCR

Figure 5:
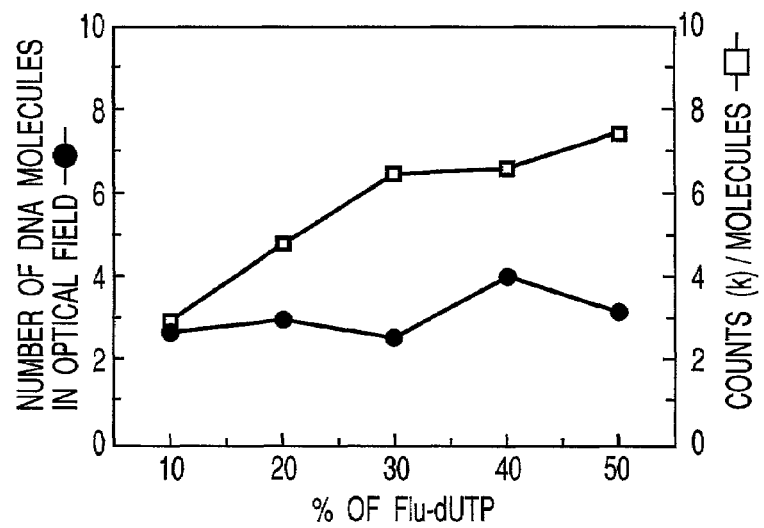
FIG. 5 is a graph showing the relationship between the marker concentration and the amount of products in PCR, obtained as a function of a percent ratio of Flu-dUTP.

FIG. 5 is a graph showing the relationship between the marker concentration and the product amount in PCR, which was obtained as a function of a percent ratio of Flu-dUTP. In the figure, a square mark indicates an average count per DNA molecule (C/M). A solid (black) mark indicates the number of DNA molecules present in the measurement region of an detection field. In FIG. 5, it is clearly shown that the fluorescent intensity per molecule (C/M) increases with an increase of Flu-dUTP. This result demonstrates that the marker concentration depends upon the concentration of Flu-dUTP. In addition, the number of DNA molecules is almost constant within the range of Flu-dUTP concentration used in the experiment. This result is consistent with electrophoretic analyses shown in FIGS. 4A and 4B. This fact demonstrates that fluoroscein does not prevent the activity of DNA synthase. When C/M values of free Flu-dUTP (monomer) and the PCR product are compared, the number of Flu-dUTP monomers incorporated into a 4000 bp DNA chain is obtained. It shows the possibility that modified nucleotides are present adjacent to each other.

(6) PCR Monitor by FCS

Figure 6:
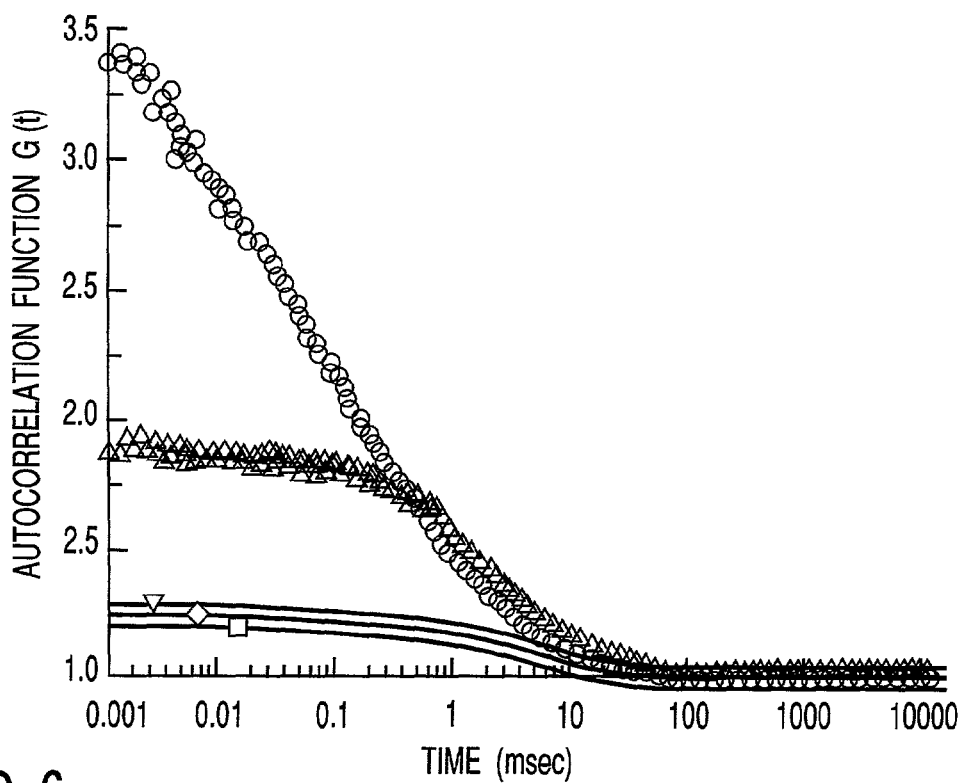
FIG. 6 is a graph showing change of the autocorrelation function with time in a PCR reaction process.

FIG. 6 is a graph showing a change of the value of autocorrelation function G(t) with time (t) during the PCR reaction, and more specifically, showing a typical change of the correlation curve with time. In the figure, a solid circular symbol, triangular symbol, reverse-triangular symbol, diamond-shaped symbol, and square symbol respectively indicate values measured at the time 10, 20, 30, 40 and 50 cycles of the nucleic acid amplification are completed. As is apparent from FIG. 6, the value (plot on the Y-axis) of the autocorrelation function at zero time-lag decreases with the number of PCR cycles. The results are due to an increase in number of DNA molecules.

Figure 7:
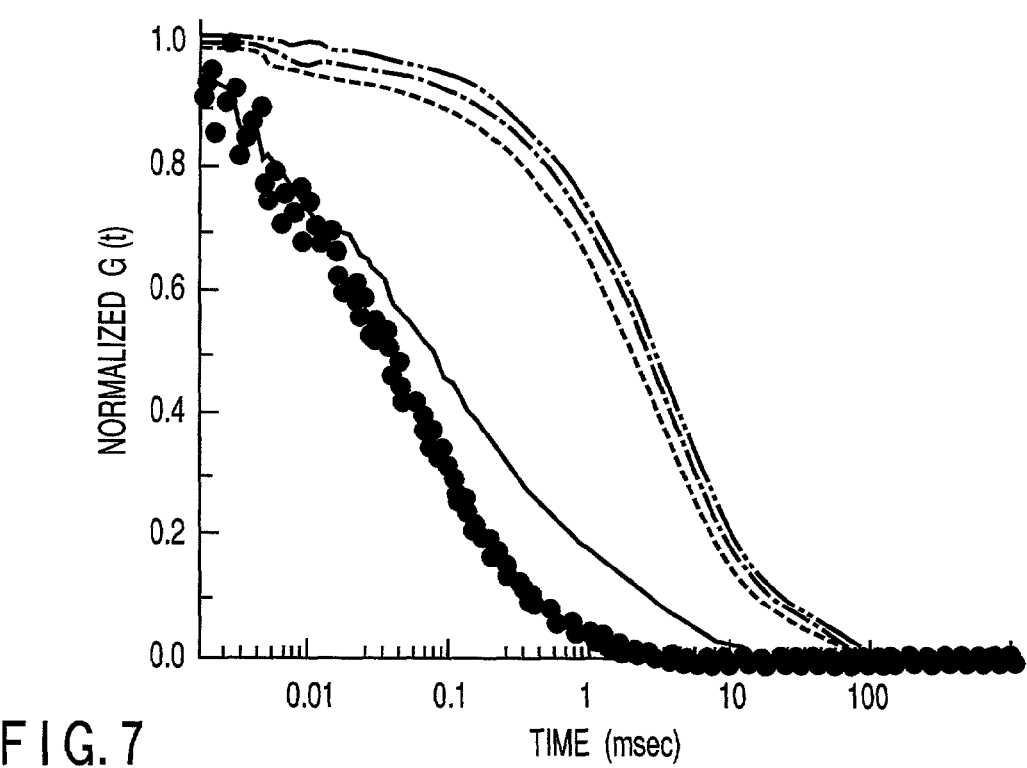
FIG. 7 is a graph obtained by normalizing each of autocorrelation functions at zero time-lag.

FIG. 7 is a graph obtained by normalizing each of the autocorrelation functions at zero time-lag. In FIG. 7, a curve of Flu-dUTP is indicated by solid circles for comparison. In the figure, a solid line, a broken line, a dotted line, a dash-dot line, and a dashed-dot-dot line respectively indicate values measured at the time 10, 20, 30, 40 and 50 cycles of the nucleic acid amplification are completed. As is apparent from FIG. 7, the autocorrelation (solid line) obtained after 10 cycles is distinct from that of Flu-dUTP. This autocorrelation was not able to be applied to a simple one-component model, but applied to a two-component model as shown in the aforementioned Equation 1. Even in the test solution obtained after 50 cycles of PCR were completed, a short diffusion-time component was detected. The short diffusion-time component is defined as non-reacted Flu-dUTP which passed through a spin column.

FIG. 8 is a graph showing the number of amplified DNA molecules in a PCR reaction solution (5 μL) versus the PCR cycle number. The total number of amplified DNA molecules was calculated by the aforementioned Equation 2.

The experiment was performed by varying an initial amount of a lambda phage DNA. In the figure, a square symbol shows the case where the initial amount of the lambda phage DNA is 200 pg ($3.75\times10^6$ copies). A circle symbol, triangular symbol, and inverted triangular symbol respectively show the cases that the initial amounts are 20 pg ($3.75\times10^5$ copies), 2 pg ($3.75\times10^4$ copies), and 0.2 pg ($3.75\times10^3$ copies), respectively.

FIG. 9 is a graph showing the relationship between the number of DNA molecules after 20 cycles and the initial number of templates. When a DNA is amplified by PCR, the DNA molecules exponentially increases before reaching a plateau. Since the template molecules is amplified to 1024 ($2^{10}$) times of the initial number, the DNA of $3.75\times10^6$ copies (corresponding to 200 pg) results in $3.75\times10^9$ copies. However, when the initial copy number is $3.75\times10^6$, $7.44\times10^9$ copies are determined by FCS measurement after 10 cycles. Similarly, when the initial copy number is $3.75\times10^5$, $0.31\times10^9$ copies are respectively determined after 10 cycles. Thus, the quantitative performance of FCS determination seems low in faithfulness (accuracy) in the early state of the test sample amplification. This is because that the number of amplified DNA is low in the detection field and many non-incorporated free labeled nucleotides are present.

In such a PCR quantification by FCS on the basis of direct fluorescence labeling, it is possible to estimate an initial concentration of the target DNA at a level of $10^3$ even after 10-cycle amplification. As is apparent from FIG. 9, however, the initial concentration of the target DNA can be determined more clearly after 20 cycles are completed. As shown in this figure, since there is a linear relationship between the initial number of DNA molecules and the number of the amplified DNA molecules, it is possible to quantify the target DNA molecule. Although the data is omitted, it was confirmed that the quantification could be made by applying another calibration curve and another DNA sequence of 500 bp. Furthermore, 20 cycles of PCR were performed by using 5 μL of test sample solution in various experiments. If the amount of the test sample solution is increased, it goes without saying that a high reproducibility can be obtained more accurately. This is the most important feature to apply this detection technique to diagnosis. It is therefore preferable that an appropriate cycle number be selected through experiments to provide a good reproducibility for saving time and materials.

As is shown in the aforementioned experiments, the present invention succeeded for the first time in applying FCS to a molecule-counting method for use in PCR with direct labeling. Furthermore, it was proven that PCR is not inhibited even if 50% of dTTP is replaced with Flu-dUTP in the case where a 4000 bp target nucleic acid is amplified. When shorter target nucleic acids, for example, 500 bp, 1000 bp, and 2000 bp are used, a more intensive fluorescence band was detected by electrophoretic analysis after 50 thermal cycles. Since a detectable marker molecule such as fluorescent molecule is bound to a substrate molecule which is used in a general PCR, this method can be easily employed in a general laboratory in the same way as in a general PCR process. The FCS assay described herein only requires slightly modifying the general PCR conditions, using a small amount (5 μL) of reaction solution as a test fluid, and performing a small-number of PCR cycles. The fluorescent marker molecule to be incorporated into a DNA molecule can be conjugated with any types of gene markers and infection markers. Therefore, the method of the present invention can be applied to such nucleic acids derived from various creatures by utilizing the previously established know-how of the PCR method.

The quantitative PCR based on FCS according to the present invention is useful in various fields because of the following reasons. First, this method has a high sensitivity, saves time and labor, and is performed by employing a reaction solution of extremely simple composition and a simple operation process. Second, the FCS measurement is performed non-invasively. Third, the test fluid after FCS measurement is completed may be used conveniently in the following experiments such as fluorescence hybridization and FISH analysis. Furthermore, a digestion reaction process with a restriction enzyme performed in a homogeneous solution can be measured by using FCS. Therefore, a point mutation and RELF etc. can be analyzed by using FCS with highly labeled DNA as described above, continually after amplification without using a isolation procedure such as column chromatography and gel chromatography. These PCR quantification methods based on FCS are applied to diagnosis and screening experiments, and further, can develop a new field for detecting molecules at a single molecular level.

As described herein, two important parameters in biological science can be obtained by using FCS. These parameters are an average number of molecules and a translational diffusion coefficient of the molecules within a detection region ($10^{-15}$ L). In the present invention, PCR products were analyzed at a single molecule level by using FCS. A specific DNA nucleotide sequence can be quantified before the PCR amplification reaches a plateau. In order to apply FCS to PCR, PCR is performed in the presence of the nucleotide monomer labeled with fluorescein 11-dUTP, which is used as a substrate in an enzymatic amplification cycle. Through the PCR reaction mentioned above, a target DNA of 4000 bp were labeled. After 10 cycles, an amplified DNA product is detected by increased diffusion time of the fluorescent molecules in the FCS detection region. The initial number of target DNA molecules in a micro-volume (5 μL) of the detection region ranged from $3.75\times10^6$ to $3.75\times10^3$ copies.

As described in the foregoing, the PCR amplification reaction in this Example is performed by using a substrate molecule labeled with a marker molecule. In addition, mobility of the marker molecules is measured. As a result, an amount of the target nucleic acids present in a test sample can be analyzed quantitatively and accurately in a simple process.

EXAMPLE 2

Amplified amount of 500 bp DNA by Rho-primer and the total number of fluorescent molecules arithmetically calculated by using FCS measurement.

This Example relates to fluorescence-labeled primer-based asymmetric PCR (referred to FA-PCR hereinafter).

(1) Implementation of Unique Asymmetric PCR

Preparation of Primer and a Mixture Solution for PCR

Asymmetric primer pairs were selected from two types of non-labeled primers, i.e., primer

```
1: 5'-GATGAGTTCGTGTCCGTACAACTGG-3'
(SEQ ID NO: 3)

and primer
```

-continued

2: 5'-GGTTATCGAAATCAGCCACAGCGC-3'
(SEQ ID NO: 4)

(manufactured by Hokkaido System Science), and two types of primers, Rho-primer 1 and Rho-primer 2 (manufactured by Takara Shuzo Co., Ltd.) which are prepared by labeling the aforementioned primers 1, 2 with a fluorescent molecule Rhodamine in combinations and concentrations shown in Table 1. Each of the primer pair was mixed with a full length lambda phage DNA (48.5 kbp, 3.2×10$^7$ Da, 1 bp=660 Da) serving as a template, a buffer (25 μL) containing 10 mM Tris-Hcl, 50 mM KCl, 1.5 mM MgCl$_2$, and 0.001% gelatin, pH8.3, together with 2.5U polymerase AmplitaqGold™ (manufactured by PE Applied Biosystems) and 0.2 mM of dNTP. The concentration of a template was varied between 1 ng/25 μL and 0.1 fg/25 μL which correspond to 1.9×10$^7$ to 9×10$^1$ molecule/25 μL.

Implementation of PCR Amplification Reaction

The PCR reaction of a nucleotide sequence of a 500 bp template DNA was performed by using a programmable thermal controller, Model PC-700 (manufactured by Astech). First, pre-incubation was performed at 96° C. for 15 minutes as a pre-denaturation step. Thereafter, a PCR cycle consisting of an annealing step at 55° C. for one minute, an elongation step at 72° C. for 2 minutes, and a denaturation step at 96° C. for one minute was performed in 50 cycles.

(2) Measurement of Amplification Reaction Results by Using FCS

Measurement of a Test Sample Mixture Solution

After 50 cycles of the amplification reaction, an appropriate amount (10 μL) of a test sample mixture solution was attached dropwise onto a cover-glass Lab-Tek (trade name, manufactured by Nalge Nunc) by pipetting. Then, the cover glass was mounted on a sample holder of an inverted FCS apparatus having a confocal optical system, ConfoCor (trade name, manufactured by Carl Zeiss). An objective lens C-Apocromat (trade name, Carl Zeiss) having a numerical aperture of 1.2 was focused on the test sample fluid on the cover-glass. In order to prevent vaporization of the test sample fluid during measurement (one minute) using argon laser excitation light, an additional similar cover-glass was placed to cover the droplet of the test-sample containing fluid attached on the cover-glass. Then, fluorescence was measured at room temperature. Incidentally, when the volume of detection region, which is a micro detection field of the FCS apparatus, was defined by measuring the diffusion time using rhodamine 6G as a reference test sample. As a result, the ratio S of the diameter to the length of the detection region was about 5.2. The volume element was 1×10$^{-15}$ L according to arithmetic calculation. After the FCS measurement, the test sample mixture was subjected to agarose gel electrophoresis, thereby identifying fractions.

Conversion of Measurement Data to Statistical Data

The intensity distribution of the laser beam on a focal point was a Gausian distribution. However, the fluorescence observation area was expressed by a nearly cylindrical shape as in FIG. 2B, and considered as such. The laser beam focused in test sample fluid forms an extremely small (micro) cylindrical field where fluorescent particles are moved in and out by the Brownian motion. As a result, the fluctuation of fluorescence intensity caused by a change in number of fluorescent particles in the micro cylindrical field can be monitored. The fluctuation of fluorescence intensity was analyzed by applying an autocorrelation function to obtain an average number of molecules within a focus region and translational diffusion time. The fluorescence autocorrelation function G(t) is as explained previously. The data analysis by FCS was performed by a computer program called "FCS ACCESS" (EVOTEC BioSystems Co., Ltd.) applying the non-linear least square method.

| Primer concentration | | | | | |
|---|---|---|---|---|---|
| Primer 1 (nM) (Rho-primer 1)$^d$ | Primer 2 (nM) (Rho-primer 2)$^d$ | Primer ratio | y$^a$ | N$^b$ | Total$^c$ |
| 800 | 400$^d$ | 1:0.5 | 0.30 | 900 | 120 |
| 800 | 40$^d$ | 1:0.05 | 0.60 | 90 | 24 |
| 800 | 4$^d$ | 1:0.005 | 0.52 | 8 | 2.1 |
| 400$^d$ | 800 | 0.5:1 | 0.35 | 863 | 140 |
| 40$^d$ | 800 | 0.05:1 | 0.21 | 76 | 8.4 |
| 4$^d$ | 800 | 0.005:1 | Nd$^e$ | 9 | Nd$^e$ |

In fitting, to reduce free parameters, τfree (0.17 ms) and τpoly (1.98 ms) were fixed to reduce free parameters. In FIG. 1, a is a yield of elongated rhodamine-labeled primer, b is an average number of fluorescent molecules in the focused field, c is a total yield calculated by using an initial concentration of a fluorescent primer and a yield of elongated rhodamine-labeled primer (y), d is a concentration of the rhodamine-labeled primer, and e indicates "not detected".

Table 1 is the results of a preliminary experiment performed in order to determine an optimum ratio of a primer set to be used in the asymmetric PCR. Six primer ratios were tested, 3 for primer 1:Rho-primer 2(800:400 nM, 800:40 nM and 800:4 nM) and 3 for Rho-prmner 1:primer 2(400:800 nM, 40:800 nM and 4:800 nM) in the presence of 1 ng of template. After 50 cycles of PCR, 10 μL of the reaction solution were set on the cover glass and then measured by FCS for 1 min. FIG. 10 shows typical fluorescence autocorrelation functions. The translational diffusion time of Rho-primer 2 ($\tau_{free}$=0.164 ms) was defined from a control sample that had not been subjected to a thermal cycle (solid circle in FIG. 10).

After 50 cycles of PCR, the autocorrelation function curve of a free Rho-primer (plotted by a circle in FIG. 10) and the autocorrelation function curve of an asymmetric PCR product were obtained by fitting data thereof in Equation 1. Then, the translational diffusion time of the free Rho-primer ($\tau_{free}$=0.164 ms) and the translational diffusion time of an amplified product DNA ($\tau_{poly}$=1.98 ms) and the yield (y=0.6) thereof were given to Equation 1. Another control sample, minus enzyme but with the thermal cycle, was also measured (data not shown), and the result was 0.169 ms. The translational diffusion time of 500-bp DNA (PCR products) was evaluated from curve fitting of autocorrelation data, giving $\tau_{poly}$=1.98 ms (a curve plotted by a square in FIG. 10). The value agreed with the 500-bp length DNA according to theoretical calculation of the translational diffusion constant of rod-like molecules. Therefore, the amplified product was well identified from the change in the autocorrelation function. Due to the different translational diffusion times of the free primer and the amplified primer, it was able to quantify the fractions of amplified products.

In the analysis, the values of $\tau_{poly}$, $\tau_{free}$ and S were fixed in the fitting to reduce the number of free parameters and clearly separate the ratio of free-to-extended primers (y). Although the free primer and PCR products were not physically separated after the thermal cycle, it was possible to measure the fractions of products by this analysis (Table 1). In the case of primer 1:Rho-primer 2 is 800 nM:40 nM, the ratio between the remaining free primer and the PCR product (y=0.6) was better than with the others. At the primer ratio of 800:400 nM, the total product of 500 bp was better than at other primer ratios. However, approximately 70% of the free primer still remained. Although it was expected that all of Rho-primer 2 would be incorporated into the PCR product at the primer ratio of 800:4 nM, only about half of the labeled primer 2 (Y=0.52) could be incorporated, so the yield of product was not better than at the ratio of 800:40 nM. Therefore, a preferable primer concentration ratio was either 800 nM:40 nM or 800 nM:40 nM. Hence, the primer concentration ratio may be selected from the range between the primer concentration ratios. In general, it is considered that a preferably primer ratio ranges from 2:1 to 20:1. Subsequently, the marker molecule was attached to the primer 1 conversely. When the PCR is performed by using Rho-primer 1 and primer 2 in a ratio of 400:800 nM, 40:800 nM, and 4:800 nM, the yield of the PCR product was 0.35 or less. Thus, it is preferable to appropriately bind the marker molecule to either of a pair of primers, depending upon a type of target nucleic acid molecule and primer molecule as well as a chain length thereof so as to increase the PCR yield.

Figure 11A:
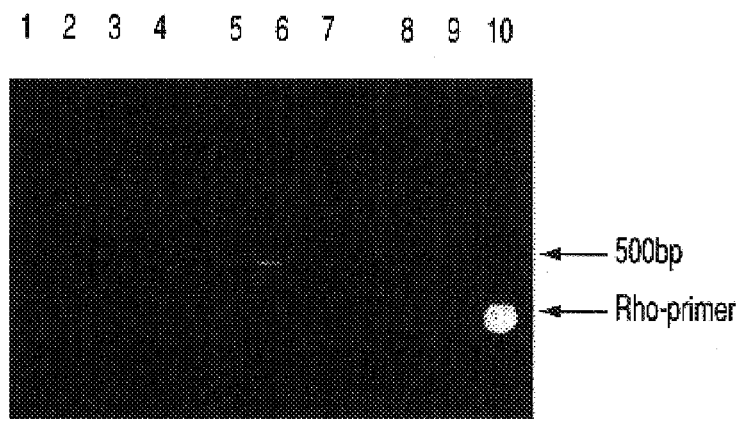
FIGS. 11A and 11B are photographs each showing the results of agarose gel electrophoresis of an amplified target product (500 bp), performed after quantitative measurement by FCS.
Figure 11B:
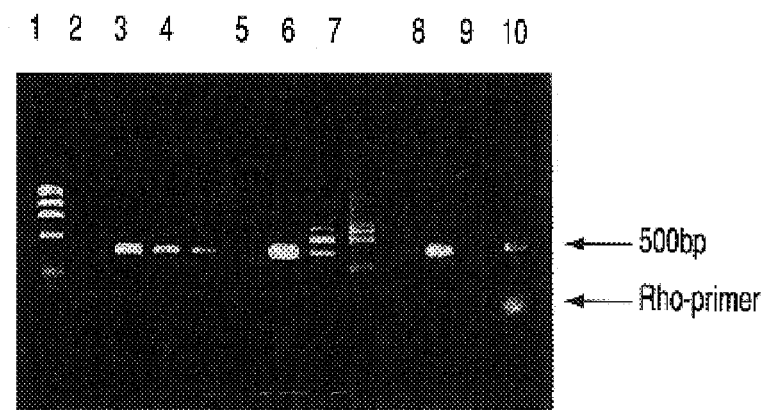

FIGS. 11A and 11B show the electrophoretic (agarose gel) results of an amplified target product of 500 bp obtained after quantitative determination by FCS measurement. Asymmetric PCR solution after 50 cycles (3 µL) was applied to 1.4% agarose gel for characterization of asymmetric PCR products with different primer ratios by agarose gel electrophoresis. FIG. 11A is a case where no ethidium bromide staining was performed. FIG. 11B is a case where ethidium bromide staining was performed. Lane 1: φX 174 marker digested with Hae III; Lane 2: a ratio of primer 1:Rho-primer 2 is 800:400 nM; lane 3: primer 1:Rho-primer 2 is 800:40 nM; lane 4: a ratio of primer 1:Rho-primer 2 is 800:4 nM; lane 5: a ratio of Rho-primer 1:primer 2 is 400:800 nM; lane 6: a ratio of Rho-primer 1:primer 2 is 40:800 nM; lane 7: a ratio of Rho-primer 1:primer 2 is 4:800 nM; lane 8: control (PCR is performed by using normal primers; and lane 9: control (using Rho-primmer 2), and control (PCR is performed by using Rho-primer 1 and Rho-primer 2). The locations of 500 bp and Rho-primer 2 are indicated by arrows. A faint and broad band between 500 bp and the Rho-primer is a bromophenol blue dye.

In all cases, the rhodamine fluorescent band of 500 bp was able to be detected without ethidium staining (FIG. 11A). The PCR products were also detected by ethidium staining performed after electrophoresis (FIG. 11B). ssDNA (single stranded DNA) of 500 bp was not clear in the gel because the fluorescent intensity of the ssDNA is less than that of dsDNA (double stranded DNA) in this staining method. In the cases of a ratio of Rho-primer 1: primer 2 is 40:800 nM and 4:800 nM, a smear and a non-specific band were detected in the gel (FIGS. 11A and 11B, lanes 5–7). Conversely, in the cases where a ratio of primer 1:Rho-primer 2 was 800:400 nM, 800:40 nM, and 800:4 nM, the 500 bp band was clearly detected, and the intensity thereof decreased as the primer ratio changed from 1:0.05 to 1:0.005 (FIGS. 11A and 11B, lanes 2–4). These results exactly corresponded to FCS determination results (Table 1). The ratio of primer 1:Rho-primer 2(800:40 nM) was used in further experiments in this work because the yield of 500 bp (y=0.6) was better than with other ratios. FCS-based, FA-PCR detection would have the advantages of quantitative accuracy and simplicity. One can detect a target gene by 1-min FCS measurement with only 10 µL of reaction solution after FA-PCR amplification. It would be interesting if a low copy number of template genes could be amplified by FA-PCR and then detected by FCS.

FIG. 12 shows the results obtained by changing an initial template concentration of a reaction solution (25 µL) prior to PCR from $1.9 \times 10^7$ to 1.9, in order to investigate the sensitivity of the aforementioned method of the present invention (an inverted open triangular symbol indicates $1.9 \times 10^7$, a solid triangular symbol indicates $1.9 \times 10^6$, an open circular symbol indicates $1.9 \times 10^5$, a solid square symbol indicates $1.9 \times 10^4$, an open diamond symbol indicates $1.9 \times 10^3$, an open inverted triangular symbol indicates $1.0 \times 10^2$, an open triangular symbol indicates $1.9 \times 10^1$, and a solid circular symbol indicates 1.9). The autocorrelation function G(t) of Rho-primer 2 shifted toward a longer correlation time (toward right hand side of FIG. 12) in proportion to an increase in template number after 50 thermal cycles. This shift corresponds to an increase of the elongated Rho-primer 2. The yield and the number of FA-PCR products were calculated by Equation 1.

Figure 13:
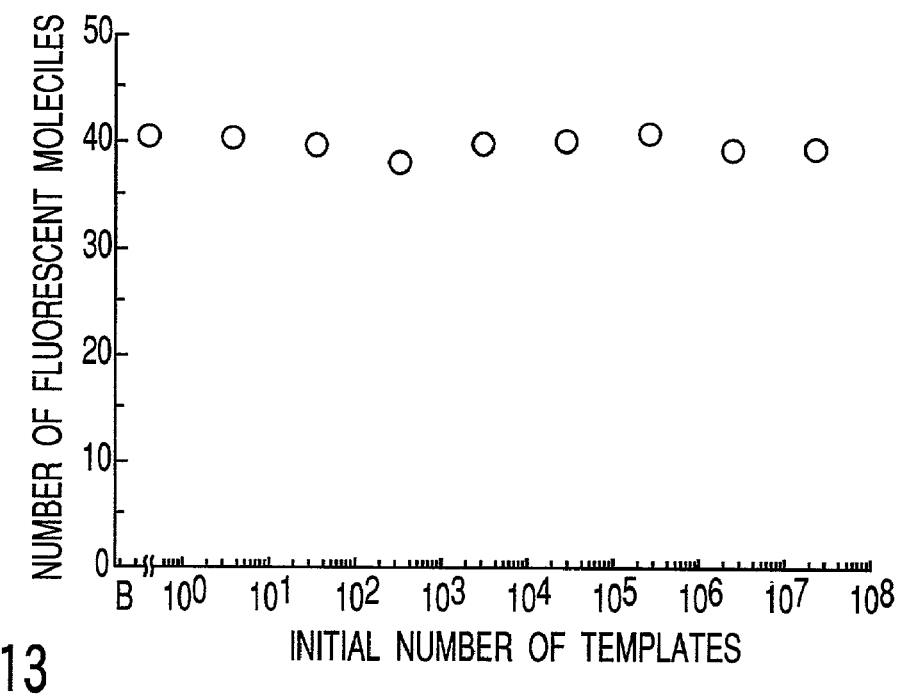
FIG. 13 shows an average number of fluorescent molecules in an optical measurement field (a micro detection field) versus the initial template concentration shown in FIG. 12.
Figure 14:
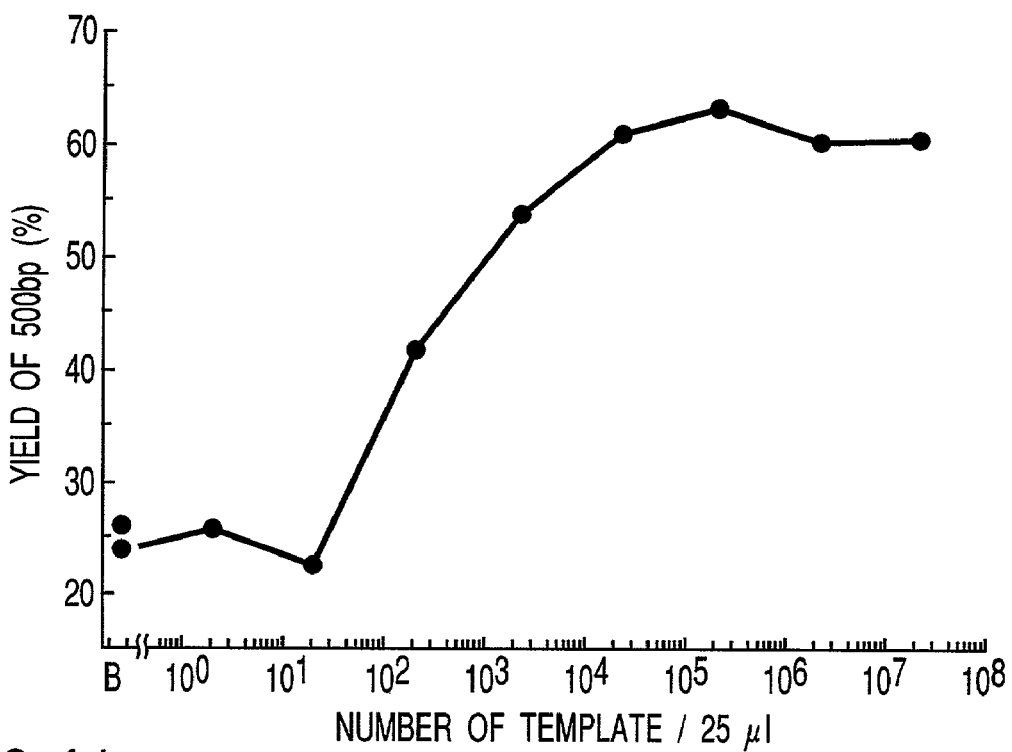
FIG. 14 is a graph showing the yield (%) of 500 bp product versus the initial template concentration.

An average number of fluorescent molecules in an optical field is shown in FIG. 13. No specific influence on the number of labeled DNA molecules was observed, so that specific or nonspecific adhesion or partitioning to the surface of the tube and/or glass was not detected in this experiment. FIG. 14 is a graph showing a yield (%) of 500 bp versus an initial template concentration. The yield of the product was dependent on the initial number of template molecules from 102 to 104 molecules/25 µL, which can be used as the quantification range. Even in the initial presence of 190 template molecules in 25 µL, the correlation decay of amplified DNA was separated, and it could be detected clearly. A plateau effect was observed with over $10^5$ template molecules after 50 cycles. Although a number of factors could have contributed to the plateau effect, it was simply related to the number of cycles. Therefore, the quantification range will be optimized by reducing the number of thermal cycles for a higher concentration of initial template molecules.

The present inventors conducted experiments to set the PCR reaction conditions more optimum. As a result, even in the case where 20 of the template DNA molecules are present in a test sample, the detection of the template DNA molecules was successfully performed. If other conditions for PCR are more optimized, it is expected easy to design the detection method in such a way that 5 template DNA molecules or less can be detected. Such experimental results suggest that only one molecule of the template DNA may be principally detectable in the method of the present invention.

Figure 15:
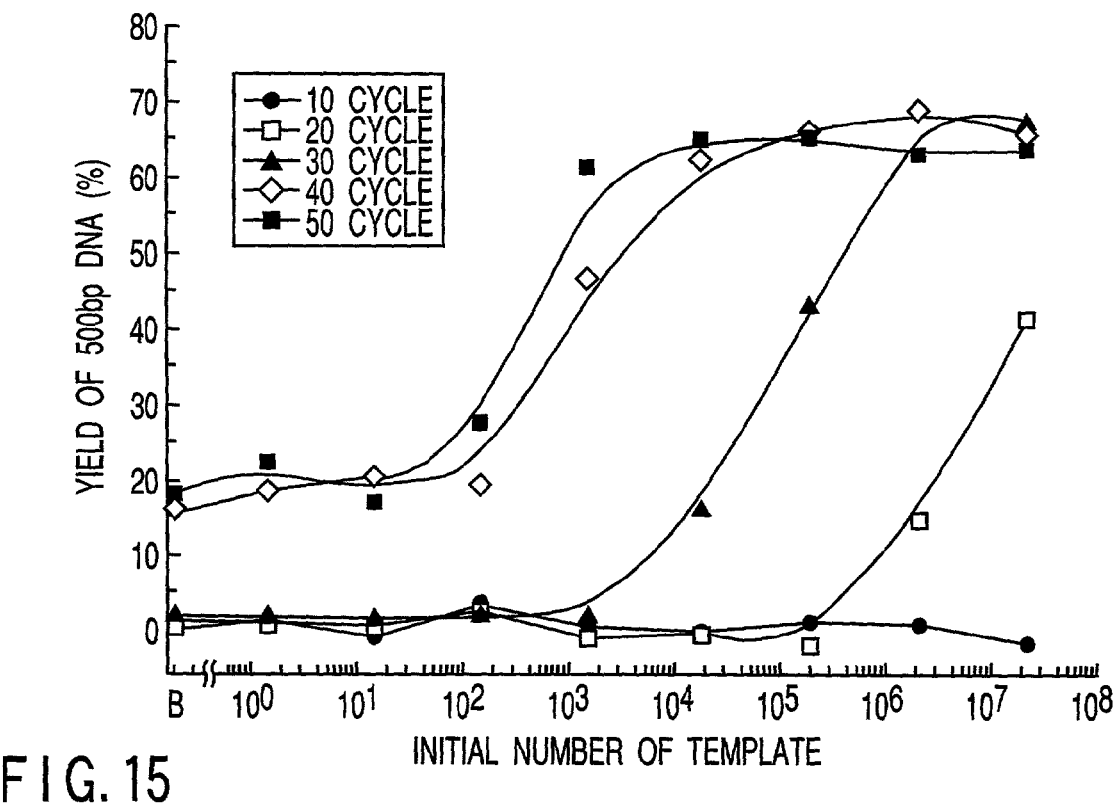
FIG. 15 is a graph showing the initial template number present in a mixed solution (25 μL) versus the yield (%) of each of PCR products obtained through different numbers of the PCR cycle.

FIG. 15 shows the initial template number present in a mixture solution of 25 µL versus the yield (%) of the PCR product with respect to each of different PCR cycles. According to the results, it is demonstrated that asymmetric PCR of 20 cycle is sufficient to quantify the target DNA in the case where the initial template molecules are present in as large number as $10^6$ or more. Similarly, 30 cycles in the range of $10^4$ to $10^6$, 40 cycles in the range of $10^2$ to $10^4$, and 50 cycles or more in the range of $10^3$ or less are possibly used in the quantification of the target DNA. In particular, when the initial templates are present in a high concentration, the quantification available range can be optimized by reducing the PCR cycle number. If data is obtained within the quantification-ensuring number of cycles as mentioned above, it is possible to determine the initial number of templates by, for example, multiplying the cycle number.

Figure 16:
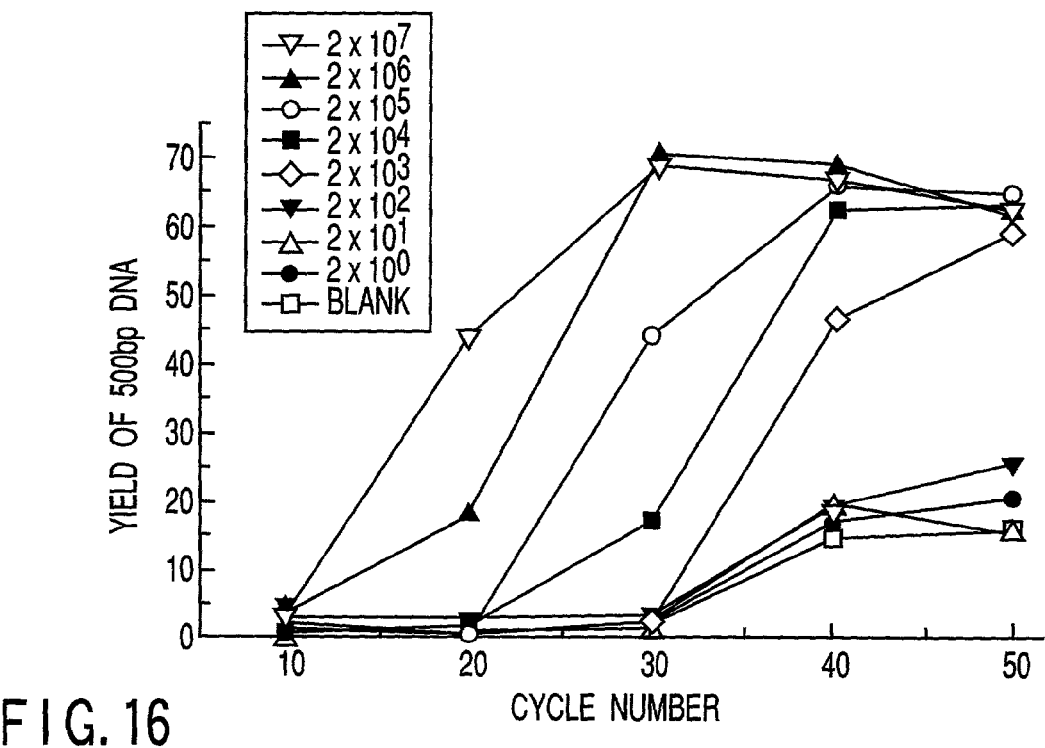
FIG. 16 is a graph showing PCR productions per initial template DNA molecule obtained through different PCR cycles, the graph being derived by dividing the measurement data of FIG. 15 per numbers of initial template DNA molecules.

FIG. 16 is a graph showing the yield of a PCR product versus the PCR cycle number with respect to the initiation number of the template DNA (data was originated from those of FIG. 15). From the results, it is demonstrated that if the templates are present in an initial number of $2\times10^3$, the determination can be performed precisely. In consideration of the data of FIG. 15, it is presumable to determine even if the templates are present in an initial number of $2\times10^2$.

As described, in this example, the PCR amplification reaction is performed by labeling a primer with a marker molecule. Furthermore, the behavior of each marker molecule is statistically analyzed through the observation within a micro detection field. It is therefore possible to accurately detect the amount of the target nucleic acid present in a test sample. In addition, since the marker molecule is bound to a second primer present relatively and significantly in a small amount, a free marker molecule is consumed certainly and completely during the PCR cycles, with the result that the Bound/Free separation of the marker molecule is not required. Accordingly, this method is easily handled, applicable to automatic operation, and reduces reagent cost.

<Discussion for Examples 1 and 2>

Recently, some reports regarding a method of detecting a target gene by use of FCS have been provided. It has been found that Nucleic acid sequence-based amplification (NASBA) was combined with FCS and has proven to be a useful detection method for human Immunodeficiency virus (HIV) diagnosis in plasma (see Oehlenschlager, F. et al, Proc. Natl. Acad. Sci. USA, 93, 12811–12816, 1996)). In the NASBA method which is one of nucleic acid amplification methods, two primers and an additional fluorescence-labeled primer serving as a probe are required in the presence of three enzymes, namely T7RNA polymerase, reverse transcriptase, and RNaseH. A simpler method has been reported by the same group, amplified probe extension (APEX) detection by FCS, but it still uses an extra fluorescence-labeled primer as a probe sequence besides a forward primer and a reverse primer set (Walter, N. G. et al., Proc. Natl. Acad. Sci. USA, 93, 12805–12810, 1996). A time shift of the autocorrelation function was observed after 26 cycles in that experiment.

A fluorescent quenching-based PCR quantification method, such as a fluorescent energy transfer analysis was previously reported (Heid, C. A. et al., Genome Res., 6, 986–994, 1996, Livak, K. J., PCR Method, Appl., 4, 357–362, 1995) and commercialized. This method employs two kinds of dyes in a single probe sequence other than a pair of PCR primers, as in the NASBA method and the APEX method described above. To design an oligonucleotide sequence of the probe, it is necessary not only to provide a nucleotide sequence that does not competing with the sequence of the primer but also to consider a melting temperature T(m). In addition, the position between donor and acceptor dyes affects the efficiency of increase of fluorescent intensity and the 5' nuclease activity of polymerase.

Another fluctuation spectroscopy method (fluorescent cross correlation spectroscopy) has been reported as a detection method for a specific target gene in a homogeneous solution (Gastro. A. et al., Anal. Chem, 67, 3915–3920, 1997, Rudolf Rigler et al., J. Biotechnology, 63, 97–109, 1998). In the cross correlation method, two probes or primers which bind to different positions of the target nucleic acid, are labeled with two types of fluorescent dyes having deferent absorption wavelength. As a result, an optical system of a measuring apparatus is inevitably large and complicated for observing that primers labeled with two types of fluorescent markers are hybridized with a single nucleic acid molecule. Although employment of the two types of dyes enables to detect an extremely small amount of the target nucleic acid sequence, this method still requires two types of fluorescent probes (primers) and therefore disadvantageous in view of convenience and reagent cost.

From the viewpoint of simplicity, the FCS-based PCR quantification method offers a major advantage over the energy-transfer and cross-correlation methods. The fidelity and sensitivity of PCR are strongly dependent on the type of enzyme (Pol I type or α type), selection of primer sequence and reaction conditions. Once these conditions can be fixed, FCS-based, FA-PCR can be immediately applied to the ordinary PCR assay with slight modification of the primer ratio. Therefore, routine PCR conditions will be easily modified to conditions for FA-PCR. Moreover, other amplification methods, such as reverse transcription (RT)-PCR can be modified for this method, and it should be possible to quantify the mRNA in single cells in the future.

In gel electrophoresis and column chromatography, the PCR product is separated from the primer and by-products. However, the target product is diluted during the electrophoresis and extraction procedures from the gel materials and then has a chance to come into contact with nuclease, leading to degradation. Conversely, the FCS method is convenient for sample collecting after measurement; a sample droplet is placed on a cover glass, and FCS is a noninvasive method, so the PCR solution is not diluted or destroyed during measurement. The FA-PCR detection method based on FCS described above, only the primer labeled with fluorescence under the reaction conditions is required without applying a physical separation method such as a gel filtration method. Although the resolution of gel electrophoresis is higher and can detect a single nucleotide difference in length, the very rapid analysis time (1 min in the Example) of FCS measurement compared with gel electrophoresis (1 h) will be advantageous for massive specimen analysis (for example, in diagnosis and screening). The screened sample from FCS can be immediately subjected to detailed analysis, such as gel electrophoresis, to confirm the FCS results or to analyze the nucleotide sequence. Moreover, the collected sample can be used in further experiments, (for example, as a hybridization probe). If one need not collect the amplified sample after FCS measurement, it can be discarded without a risk of carryover contamination because FCS is a non-contact measurement method.

As FCS is noninvasive and allows direct measurement, the PCR volume is dependent on the measurement volume needed for FCS. Current measurements of FCS were carried out with a 10-μL sample volume, though the sample volume can theoretically be reduced to a volume element of the order of $10^{-15}$ L. However, the PCR volume can be reduced to 1 μL, and thus, it would have a great advantage in comparison with other methods from an economical point of view. Moreover, FCS is based on fluorescence microscopy, and the detection field is set on the objective, so that this method will be able to quantify specific RNA and DNA from in situ PCR.

The present inventors used a two-component model for analysis of the PCR solution and obtained good results. However, many DNA species might be present in other experiments. In such cases, species of DNA can be well separated by conventional gel electrophoresis. Although the gap in the correlation curve from the model function to observed data of FCS could suggest some other components distributed in the solution, the simple two-component model seems to be the limit in such cases. Consequently, when more detailed quantitative analysis is necessary, multicomponent FCS analysis (13) should be developed to obtain the distribution function using a computer program such as CONTIN (Max Planck Institute for Biophysical Chemistry, Göttingen, Germany).

Without using a physical separation procedure, this method is noninvasive, non-contact and uses a small sample volume. Physical handling of such a small sample volume can be done by using a capillary tube or by using a small sample pit on a glass surface covered by a thin cover glass or by film for on-line analysis. With these properties and improvements, it is straightforward to use, and the process used to monitor amplification is simple (on-line monitoring) and can be used with an automatic detection system (robotics). The inventor of the present invention therefore con clude that FCS-based, FAPCR quantification has advantages in terms of sensitivity, quantitative precision and simplicity. Since a spatial (three-dimensional) resolution ability of the microscopy to be used is the resolution of FCS, it is easy to measure by spatially selecting a part of a cell. For example, an intracellular molecular transportation of a fusion protein can be measured by using GFP (green fluorescent protein). Furthermore, it is expected that the method of the present invention will be useful not only for rapid screening, but also to open a new field of molecular diagnosis.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A method of analyzing a target nucleic acid by applying a nucleic acid amplification reaction to a test solution containing the target nucleic acid, wherein an amplified product is labeled with a marker molecule, said method comprises:
   (a) performing a nucleic acid amplification reaction of the target nucleic acid in a test solution containing a forward primer and a reverse primer, a substrate comprising nucleotides, a nucleic acid polymerase and a target nucleic acid, wherein the forward primer is in a lower amount than the reverse primer or the reverse primer is in a lower amount than the forward primer, and the primer present in a lower amount is labeled with a marker molecule capable of generating a detectable signal to form a labeled primer, the nucleic acid amplification reaction being performed until the primer present in a lower amount is consumed;
   (b) measuring a signal from the marker molecule in the test solution after initiation of the nucleic acid amplification reaction;
   (c) evaluating a fluctuation motion of the labeled primer and the amplified nucleic acid which is labeled with the marker molecule, in the test solution on the basis of the signal detected;
   (d) determining a number of cycles of the nucleic acid amplification reaction performed until the labeled primer has been completely consumed, and a yield of the amplified nucleic acid which is labeled with the marker molecule, based on an evaluation result of the step (c); and
   (e) quantifying an initial amount of the target nucleic acid on the basis of the number of cycles of the nucleic acid amplification reaction and the yield of the amplified nucleic acid which is labeled with the marker molecule.

2. A method according to claim 1, wherein the measurement step includes a step of measuring an amount of the marker molecule present in a predetermined micro detection field, said marker molecule being contained in the labeled primer attached to the target nucleic acid.

3. A method according to claim 2, wherein, in the measurement step, the measurement is performed in a fluid.

4. A method according to claim 3, wherein the evaluation step comprises a measurement which is effected by fluorescence correlation spectroscopy.

5. A method according to any one of claims 1 to 4, wherein the quantifying of the target nucleic acid includes determining the presence and absence of the marker molecule of the labeled primer attached to the target nucleic acid and incorporated into products of the nucleic acid amplification reaction on the basis of the evaluation results.

6. The method according to any one of claims 1 to 4, wherein the quantifying of the target nucleic acid includes determining the number of the labeled primer attached to the target nucleic acid and incorporated into products of the nucleic acid amplification reaction on the basis of the evaluation results.

7. A method according to any one of claims 1 to 4, wherein the number of labeled primer molecules is known.

8. A method according to claim 1, wherein the mixing ratio of the forward primer and the reverse primer is in a range of 2:1 to 20:1.

9. A method according to claim 8, wherein the mixing ratio of the forward primer and the reverse primer is in a range of 800 nM: 400 nM to 800 nM 40 nM.

* * * * *

UNITED STATES PATENT AND TRADEMARK OFFICE
CERTIFICATE OF CORRECTION

PATENT NO.      : 7,115,365 B2
APPLICATION NO. : 09/325189
DATED           : October 3, 2006
INVENTOR(S)     : Kinjo It is certified that error appears in the above-identified patent and that said Letters Patent is hereby corrected as shown below:

Title Page, Under Notice: Left Column, delete "This patent is subject to a terminal disclaimer."

Signed and Sealed this

Sixth Day of March, 2007

JON W. DUDAS
*Director of the United States Patent and Trademark Office*